US009180181B2

(12) United States Patent
Olsen et al.

(10) Patent No.: US 9,180,181 B2
(45) Date of Patent: *Nov. 10, 2015

(54) H3 INFLUENZA A VIRUS

(71) Applicant: Wisconsin Alumni Research Foundation, Madison, WI (US)

(72) Inventors: Christopher W. Olsen, Madison, WI (US); Gabriele A. Landolt, Fort Collins, CO (US); Alexander I. Karasin, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/255,719

(22) Filed: Apr. 17, 2014

(65) Prior Publication Data

US 2014/0377296 A1    Dec. 25, 2014

Related U.S. Application Data

(60) Continuation of application No. 13/839,111, filed on Mar. 15, 2013, now Pat. No. 8,784,838, which is a continuation of application No. 12/503,712, filed on Jul. 15, 2009, now Pat. No. 8,535,685, which is a division of application No. 11/033,248, filed on Jan. 11, 2005, now Pat. No. 7,572,620.

(51) Int. Cl.
| | | |
|---|---|---|
| *A61K 39/145* | (2006.01) | |
| *C07K 14/005* | (2006.01) | |
| *C12R 1/91* | (2006.01) | |
| *C12N 7/00* | (2006.01) | |
| *G01N 33/569* | (2006.01) | |
| *A61K 39/12* | (2006.01) | |
| *A61K 39/00* | (2006.01) | |

(52) U.S. Cl.
CPC .............. *A61K 39/145* (2013.01); *A61K 39/12* (2013.01); *C07K 14/005* (2013.01); *C12N 7/00* (2013.01); *C12R 1/91* (2013.01); *G01N 33/56983* (2013.01); *A61K 2039/525* (2013.01); *A61K 2039/5254* (2013.01); *A61K 2039/54* (2013.01); *C12N 2760/16121* (2013.01); *C12N 2760/16122* (2013.01); *C12N 2760/16134* (2013.01); *G01N 2333/11* (2013.01)

(58) Field of Classification Search
None
See application file for complete search history.

(56) References Cited

U.S. PATENT DOCUMENTS

| | | | |
|---|---|---|---|
| 4,920,213 A | 4/1990 | Dale et al. | |
| 5,925,359 A | 7/1999 | Van Woensel et al. | |
| 6,406,843 B1 | 6/2002 | Skeeles et al. | |
| 6,649,169 B2 | 11/2003 | Dowling | |
| 7,572,620 B2 * | 8/2009 | Olsen et al. | 435/235.1 |
| 7,682,619 B2 | 3/2010 | Dubovi | |
| 7,959,929 B2 | 6/2011 | Crawford et al. | |
| 8,535,685 B2 * | 9/2013 | Olsen et al. | 424/209.1 |
| 8,697,089 B2 * | 4/2014 | Olsen et al. | 424/209.1 |
| 8,784,838 B2 * | 7/2014 | Olsen et al. | 424/209.1 |
| 2004/0146530 A1 | 7/2004 | Sharma | |
| 2004/0223976 A1 | 11/2004 | Bianchi et al. | |
| 2006/0153871 A1 | 7/2006 | Olsen et al. | |
| 2007/0253981 A1 | 11/2007 | Dubovi | |
| 2010/0062014 A1 | 3/2010 | Olsen et al. | |
| 2013/0195906 A1 | 8/2013 | Olsen et al. | |
| 2013/0209509 A1 | 8/2013 | Olsen et al. | |

FOREIGN PATENT DOCUMENTS

| | | |
|---|---|---|
| EP | 726316 A2 | 8/1996 |
| JP | 2002-522078 A | 7/2002 |
| JP | 2006-067979 A | 3/2006 |
| NO | WO-01/60849 A2 | 8/2001 |
| WO | WO-2004-112831 A2 | 12/2004 |

OTHER PUBLICATIONS

Daly et al. 1996, J Gen Virol vol. 77 pp. 661-671.*
Peek et al., J Vet Intern Med 2004 pp. 132-134.*
UF News Apr. 22, 2004.*
Dubovi et al. AAVLD 2004 p. 158.*
"U.S. Appl. No. 11/033,248, Declaration Under 37 C.F.R. 1.131 filed Apr. 18, 2008", 6 pgs.
"U.S. Appl. No. 11/033,248, Declaration Under 37 C.F.R. 1.132 by Anne Koch dated Apr. 21, 2008", 2 pgs.
"U.S. Appl. No. 11/033,248, Declaration Under 37 C.F.R. 1.132 filed Apr. 18, 2008", 4 pgs.
"U.S. Appl. No. 11/033,248, Non-Final Office Action mailed Sep. 4, 2008", 8 pgs.
"U.S. Appl. No. 11/033,248, Notice of Allowance mailed Mar. 31, 2009", 6 pgs.
"U.S. Appl. No. 11/033,248, Response filed Jan. 5, 2009 to Office Action mailed Sep. 4, 2008", 8 pgs.
"U.S. Appl. No. 11/033,248, Response filed Aug. 29, 2007 to Restriction Requirement mailed Jun. 26, 2007", 9 pgs.
"U.S. Appl. No. 11/033,248, Response to Non-Final Office Action mailed Nov. 21, 2007.", 12 pgs.
"U.S. Appl. No. 11/033,248, Response to Request for Information Under 37 C.F.R. 1.105 filed Apr. 21, 2008", 1 pg.
"U.S. Appl. No. 11/033,248, Restriction Requirement mailed Jun. 26, 2007", 8 pgs.
"U.S. Appl. No. 11/033,248, Non-Final Office Action mailed Nov. 21, 2007", 10 pgs.
"U.S. Appl. No. 12/503,712, Examiner Interview Summary mailed Jun. 21, 2012", 2 pgs.
"U.S. Appl. No. 12/503,712, Non Final Office Action mailed Jun. 21, 2012", 7 pgs.
"U.S. Appl. No. 12/503,712, Notice of Allowance mailed Feb. 8, 2013", 6 pgs.
"U.S. Appl. No. 12/503,712, Notice of Allowance mailed May 15, 2013", 10 pgs.
"U.S. Appl. No. 12/503,712, Preliminary Amendment mailed Aug. 11, 2009", 3 pgs.
"U.S. Appl. No. 12/503,712, Preliminary Amendment mailed Nov. 13, 2009", 3 pgs.

(Continued)

*Primary Examiner* — Mary E Mosher
*Assistant Examiner* — Myron Hill
(74) *Attorney, Agent, or Firm* — Schwegman Lundberg & Woessner, P.A.

(57) ABSTRACT

The invention provides an isolated H3 equine influenza A virus, as well as methods of preparing and using the virus, and genes or proteins thereof.

9 Claims, 13 Drawing Sheets

(56) References Cited

OTHER PUBLICATIONS

"U.S. Appl. No. 12/503,712, Response filed Apr. 2, 2012 to Restriction Requirement mailed Mar. 1, 2012", 9 pgs.
"U.S. Appl. No. 12/503,712, Response filed Apr. 2, 2013 to Non Final Office Action mailed Feb. 8, 2013", 9 pgs.
"U.S. Appl. No. 12/503,712, Response filed Sep. 21, 2012 to Non Final Office Action mailed Jun. 21, 2012", 11 pgs.
"U.S. Appl. No. 12/503,712, Restriction Requirement mailed Mar. 1, 2012", 7 pgs.
"U.S. Appl. No. 13/839,111, Corrected Notice of Allowability mailed Jun. 23, 2014", 4 pgs.
"U.S. Appl. No. 13/839,111, Non Final Office Action mailed Aug. 12, 2013", 10 pgs.
"U.S. Appl. No. 13/839,111, Notice of Allowance mailed Jan. 2, 2014", 10 pgs.
"U.S. Appl. No. 13/839,111, PTO Response to 312 Amendment mailed Apr. 18, 2014", 2 pgs.
"U.S. Appl. No. 13/839,111, Response filed Nov. 12, 2013 to Non Final Office Action mailed Aug. 12, 2013", 12 pgs.
"U.S. Appl. No. 13/842,168, Examiner Interview Summary mailed Dec. 5, 2013", 3 pgs.
"U.S. Appl. No. 13/842,168, Non Final Office Action mailed May 24, 2013", 10 pgs.
"U.S. Appl. No. 13/842,168, Notice of Allowance mailed Oct. 2, 2013", 12 pgs.
"U.S. Appl. No. 13/842,168, Response filed Aug. 22, 2013 to Non Final Office Action mailed May 24, 2013", 9 pgs.
"Australian Application Serial No. 2006200484, Office Action mailed Feb. 17, 2012", 3 pgs.
"Australian Application Serial No. 2006200484, Response filed Jan. 17, 2013 to Office Action mailed Feb. 17, 2012", 25 pgs.
"Australian Application Serial No. 2006200484, Response filed Apr. 17, 2013 to Subsequent Examiners Report mailed Jan. 25, 2013", 15 pgs.
"Australian Application Serial No. 2006200484, Subsequent Examiners Report mailed Jan. 25, 2013", 4 pgs.
"Australian Application Serial No. 2013219230, Examination Report No. 1 mailed Mar. 16, 2015", 5 pgs.
"Australian Application Serial No. 2013219230, Response filed May 15, 2015 to Examination Report No. 1 mailed Mar. 16, 2015", 10 pgs.
"Canadian Application Serial No. 2,535,127, Office Action mailed Feb. 10, 2015", 6 pgs.
"Canadian Application Serial No. 2,535,127, Office Action mailed Oct. 4, 2012", 3 pgs.
"Canadian Application Serial No. 2,535,127, Office Action mailed Nov. 8, 2013", 5 pgs.
"Canadian Application Serial No. 2,535,127, Response filed Apr. 4, 2013 to Office Action mailed Oct. 4, 2012", 14 pgs.
"Canadian Application Serial No. 2,535,127, Response filed May 8, 2014 to Office Action mailed Nov. 8, 2013", 28 pgs.
"DQ222913—Influenza A virus (A/equine/Wisconsin/1/03 (H3N8)) hemagglutinin (HA) gene, complete cds", Database GenBank, [Online]. Retrieved from the Internet: <http://www.ncbi.nlm.nih.gov/entrez/viewer.fcgi?db=nucleotide&val=78057300>, (Oct. 29, 2005), 2 pgs.
"DQ222914—Influenza A Virus (A/equine/Wisconsin/1/03 (H3N8)) neuraminidase (NA) gene, complete cds", Database GenBank, [Online]. Retrieved from the Internet: <http://www.ncbi.nlm.nih.gov/entrez/viewer.fcgi?db=nucleotide&val=78057302>, (Oct. 29, 2005), 2 pgs.
"DQ222915—Influenza A virus (A/equine/Wisconsin/1/03 (H3N8)) nucleoprotein (NP) gene, complete cds", Database GenBank, [Online]. Retrieved from the Internet: <http://www.ncbi.nlm.nih.gov/entrez/viewer.fcgi?db=nucleotide&val=78057304>, (Oct. 29, 2005), 2 pgs.
"DQ222916 Influenza A virus (A/equine/Wisconsin/1/03 (H3N8)) matrix protein 2 (M2) and matrix protein 1 (M1) genes, complete cds", Database GenBank, [Online], Retrieved from the Internet: <http://www.ncbi.nlm.nih.gov/nuccore/dq222916>, (Oct. 29, 2005), 2 pgs.
"DQ222917—Influenza A virus (A/equine/Wisconsin/1/03 (H3N8)) nonstructural protein 2 (NS2) and nonstructural protein 1 (NS1) genes, complete cds", Database GenBank, [Online]. Retrieved from the Internet: <http://www.ncbi.nlm.nih.gov/entrez/viewer.fcgi?db=nucleotide&val=78057309>, (Oct. 29, 2005), 2 pgs.
"DQ222918—Influenza A virus (A/equine/Wisconsin/1/03 (H3N8)) polymerase acidic protein 2 (PA) gene, complete cds", Database GenBank, [Online]. Retrieved fromt the Internet: <http://www.ncbi.nlm.nih.gov/nuccore/dq222918>, (Oct. 29, 2005), 2 pgs.
"DQ222919—Influenza A virus (A/equine/Wisconsin/1/03H3N8)) polmerase subunit (PB1) gene, complete cds", Database GenBank, [Online]. Retrieved from the Internet: <http://www.ncbi.nlm.nih.gov/entrez/viewer.fcgi?db=nucleotide&val=78057314>, (Oct. 29, 2005), 2 pgs.
"DQ222920—Influenze A virus (A/equine/Wisconsin/1/03 (H3N8)) polymerase subunit PB2 (PB2) gene, complete cds", Database GenBank, [Online]. Retrieved from the Internet: <http://www.ncbi.nlm.nih.gov/entrez/viewer.fcgi?db=nucleotide&val=78057316>, (Oct. 24, 2005), 2 pgs.
"Hemagglutinin precursor [Influenza A virus (A/equine/Kentucky/5/2002 (H3N8))]", GenBank Accession No. AAX23575, (Mar. 12, 2005), 1 pg.
"Influenza A virus (A/equine/Florida/1/93(H3N8)) hemagglutinin precursor (HA) gene, complete cds", Database GenBank, accession No. L39916, [Online]. Retrieved from the Internet: <http://www.ncbi.nim.nih.gov/nnuccore/L39916>, (Nov. 1, 2004).
"Japanese Applicatiion Serial No. 2006-089224, Examiners Decision of Final Refusal mailed Sep. 4, 2012", (w/ English Translation), 14 pgs.
"Japanese Application Serial No. 2006-089224, First Office Action mailed Jun. 28, 2011", (w/ English Translation), 12 pgs.
"Japanese Application Serial No. 2006-089224, Office Action mailed Jan. 29, 2013", 1 pg.
"Japanese Application Serial No. 2006-089224, Office Action mailed May 13, 2014", (w/ English Translation), 14 pgs.
"Japanese Application Serial No. 2006-089224, Office Action mailed Nov. 25, 2014", (w/ English Translation), 10 pgs.
"Japanese Application Serial No. 2006-089224, Response filed Jan. 4, 2013 to Office Action mailed Sep. 4, 2012", (w/ English Translation of Amended Claims), 9 pgs.
"Japanese Application Serial No. 2006-089224, Response filed Dec. 28, 2011 to First Office Action mailed Jun. 28, 2011", (w/ English Translation of Amended Claims), 10 pgs.
"Japanese Application Serial No. 2013-000098, Amendment filed Jan. 10, 2013", (w/ English Translation of Amended Claims), 17 pgs.
"Japanese Application Serial No. 2013-000098, Office Action mailed Jun. 24, 2014", (w/ English Translation), 11 pgs.
"Japanese Application Serial No. 2013-000098, Response filed Oct. 24, 2014 to Office Action mailed Jun. 24, 2014", (w/ English Translation of Amended Claims), 15 pgs.
"Japanese Application Serial No. 2013243480, Examiners Decision of Final Refusal mailed Apr. 7, 2015", (w/ English Translation), 11 pgs.
"Korean Application Serial No. 10-2006-22670, Notice of Preliminary Rejection mailed Jul. 8, 2014", (w/ English Translation), 5 pgs.
"Korean Application Serial No. 10-2006-22670, Office Action mailed Feb. 26, 2014", (w/ English Translation), 13 pgs.
"Korean Application Serial No. 10-2006-22670, Office Action mailed Jul. 25, 2013", (w/ English Translation), 24 pgs.
"Korean Application Serial No. 10-2006-22670, Office Action mailed Nov. 2, 2012", (w/ English Translation), 22 pgs.
"Korean Application Serial No. 10-2006-22670, Response filed Mar. 18, 2013 to Office Action mailed Nov. 2, 2012", (w/ English Translation of Amended Claims), 32 pgs.
"Korean Application Serial No. 10-2006-22670, Response filed Sep. 5, 2014 to Notice of Preliminary Rejection mailed Jul. 8, 2014", 13 pgs.
"Korean Application Serial No. 10-2006-22670, Response filed Oct. 25, 2013 to Office Action mailed Jul. 25, 2013", w/English Translation, 39 pgs.
"Korean Application Serial No. 10-2013-128074, Notice of Preliminary Rejection mailed Dec. 10, 2013", (w. English Translation), 4 pgs.

(56) References Cited

OTHER PUBLICATIONS

"Korean Application Serial No. 10-2013-128074, Response filed Sep. 11, 2014 to Notice of Preliminary Rejection mailed Dec. 10, 2013", (w/ English Translation of Pending Claims), 7 pgs.

"Mexican Application No. PA/a/2006/001355, Response filed Sep. 22, 2010 to Office Action mailed Jul. 22, 2010", (w/ English Translation of Claims), 39 pgs.

"Mexican Application Serial No. PA/a/2006/001355 Office Action mailed Jul. 22, 2010", (w/ English Translation), 3 pgs.

"Mexican Application Serial No. PA/a/2006/001355, Office Action mailed Sep. 29, 2010", (w/ English Translation), 3 pgs.

"Mexican Application Serial No. PA/a/2006/001355, Response Nov. 30, 2010 to Office Action mailed Sep. 29, 2010", (w/ English Translation of Claims), 21 pgs.

"Mexican Application Serial No. PA/a/2006/001355, Notice of Allowance mailed Dec. 22, 2010", 2. pgs.

"Regional Reports of Outbreaks Diagnosed and Domestic Vaccination Policies", *Proceedings of the Fourth International Meeting of OIE and WHO Experts on Control of Equine Influenza*, (Havemeyer Foundation Monograph Series No. 7), Mumford, J. A., et al., Editors, R & W Publications Limited, (2003), 6-14.

"Session 3: Vaccine Strain Selection Scheme", *Proceedings of the Fourth International Meeting of OIE and WHO Experts on Control of Equine Influenza*. (Havemeyer Foundation Monograph Series No. 7), Mumford, J. A. et al., Editors, R & W Publications Limited, (2003), 21-29.

"Session 4: Vaccines", *Proceedings of the Fourth International Meeting of OIE andd WHO Experts on Control of Equine Influenza*, Havemeyer Foundation Monograph Series No. 7), Mumford, J. A., Editors, et al., R & W Publications Limited, (2003), 31-44.

"Session 6: International Movement and Disease Control", *Proceedings of the Fourth International Meeting of OIE and WHO Experts on Control of Equine Influenza*, (Havemeyer Foundation Monograph Series No. 7), Mumford, J. A., et al., Editors, R & W Publications Limited, (2003), 55-60.

"Session 7: The Way Ahead", *Proceedings of the Fourth International Meeting of OIE and WHO Experts on Control of Equine Influenza*, (Havemeyer Foundation Monograph Series No. 7), Mumford, J. A., et al., Editors, R & W Publications Limited, (2003), 61-65.

"UF Researchers: Equine Influenza Virus Likely Involved in Recent Respiratory Disease Outbreak in Racing Greyhounds", UF News, [online]. [retrieved on Sep. 20, 2004]. Retrieved from the Internet: <URL: http://www.napa.ufl.edu/ 2004news/racedogflu.htm>, (2004), 2 pgs.

"University of Pittsburgh Researchers Develop Virus for First Intranasal Equine Influenza Vaccine", UPMC, University of Pittsburgh News Bureau, (Nov. 23, 1999), 1-3.

Barnett, D.V.M., D. C., "Vigilance and Vaccination: The Best Defenses Against Costly Equine Influenza", (prior to Jan. 11, 2005), 4 pgs.

Bridgen, A., "Rescue of a Segmented Negative-Strand RNA Virus Entirely From Cloned Complementary DNAs", *Proc. Natl. Acad. Sci. USA*, 93, (1996), 15400-15404.

Castrucci, M. R, et al., "Attenuation of Influenza A Virus by Insertion of a Foreign Epitope into the Neuraminidase", *Journal of Virology*, 66(8), (1992), 4647-4653.

Castrucci, M. R, et al., "Reverse genetics system for generation of an influenza A virus mutant containing a deletion of the carboxyl-terminal residue of M2 protein.", *J Virol.*, 69(5), (May 1995), 2725-8.

Conzelmann, K.-K., "Genetic Engineering of Animal RNA Viruses", *Trends in Microbiology*, 4(10), (1996), 386-393.

Conzelmann, K.-K., "Genetic manipulation of non-segmented negative-strand RNA viruses", *Journal of General Virology*, 77(Pt. 3), (Mar. 1996), 381-389.

Conzelmann, K.-K., "Nonsegmented Negative-Strand RNA Viruses: Genetics and Manipulation of Viral Genomes", *Annu. Rev. Genet.*, 32, (1998), 123-162.

Conzelmann, K.-K., "Rescue of Synthetic Genomic RNA Analogs of Rabies Virus by Plasmid-Encoded Proteins", *Journal of Virology*, 68(2), (1994), 713-719.

Crawford, P. C, et al., "Transmission of Equine Influenza Virus to Dogs", Science Express, 310(5747), http://www.sciencemag.org/content/310/5747/482.long, (Published Online Sep. 29, 2005), 482-485.

Crawford, P. C, et al., "Transmission of equine influenza virus to dogs", *Science*, 310(5747), (Oct. 21, 2005), 482-485.

Crawford, P. C., et al., "Transmission of Equine Influenza Virus to Dogs", *Science*, 310, (2005), 482-485.

Daly, J. M., et al., "Antigenic and genetic evolution of equine H3N8 influenza A virsuses", *Journal of General Virology*, vol. 77, (1996), 661-671.

Daly, J. M., et al., "Influenza Infections", In: Equine Respiratory Diseases, Lekeux, P., Editor, International Veterinary Information Services, (Nov. 13, 2001), 8 pgs.

Enami, M., "An Influenza Virus Containing Nine Different RNA Segments", *Virology*, 185(1), (1991), 291-298.

Enami, M., et al., "High-Efficiency Formation of Influenza Virus Transfectants", *Journal of Virology*, 65(5), (1991), 2711-2713.

Filaroski, P. D., "Equine Flu Hits Jacksonville Greyhounds", The Business Journal of Jacksonville, Apr. 22, 2004, http://jacksonville.bizjournals.com/jacksonville/stories/2004/04/19/daily33.html, (observed Apr. 23, 2004), 2 pgs.

Fodor, E., "Rescue of Influenza A Virus from Recombinant DNA", *Journal of Virology*, 73(11), (1999), 9679-9682.

Goto, H., "Mutations Affecting the Sensitivity of the Influenza Virus Neuraminidase to 4-Guanidino-2, 4-dideoxy 2, 3-dehydro-N-acetylneuraminic Acid", *Virology*, 238, (1997), 265-272.

Hatta, M., et al., "Molecular Basis for High Virulance of Hong Kong H5N1", *Science*, 293(5536), (Sep. 7, 2001), 1840-1842.

Horimoto, T., et al., "Reverse Genetics Provides Direct Evidence for a Correction of Hemagglutinin Cleavability and Virulence of an Avian Influenza A Virus", *Journal of Virology*, 68(5), (1994), 3120-3128.

Huddleston, J. A., et al., "The Sequence of the Nucleoprotein Gene of Human Influenza A Virus, Strain A/NT/60/68", *Nucleic Acids Research*, 10(3), (1982), 1029-1038.

Kendal, A. P., et al., "Further Studies of the Neuraminidase Content of Inactivated Influenza Vaccines and the Neuraminidase Antibody Responses After Vaccination of Immunologically Primed and Unprimed Populations", *Infection and Immunity*, 29(3) (Sep. 1980), 966-971.

Kovesdi, I., et al., "Adenoviral Vectors for Gene Transfer", *Current Opinion in Biotechnology*, 8(5), (Oct. 1997), 583-589.

Lai, A. C. K., et al., "Alternative Circulation of Recent Equine-2 Influenza Viruses (H3N8) From Two Distinct Lineages in the United States", *Virus Research*, 100(2), (2004), 159-164.

Lai, A., "Introduction; Genetic Analysis Based on Nucleotide Sequence of the HA and Other Genes", *Proceedings of the Fourth International Meeting of OIE and WHO Experts on Control of Equine Influenza*, Havemeyer Foundation Monograph Series No. 7), Mumford, J. A., et al., Editors, R & W Publications Limited, (2003), 16-19.

Landolt, G., et al., "Growth Characteristics of Influenza A Viruses in Primary Canine Respiratory Cells" *Proceedings of the 85th Annual Meeting of the Research Workers in Animal Diseases (CRWAD)*, (Abstract No. P92), (2004), p. 104.

Lawson, N. D., "Recombinant Vesicular Stomatitis Viruses From DNA", *Proc. Natl. Acad. Sci. USA*, 92(10), (1995), 4477-4481.

Li, S., et al., "Electroporation of Influenza Virus Ribonucleoprotein Complexes for Rescue of the Nucleoprotein and Matrix Genes", *Virus Research*, 37(2), (1995), 153-161.

Lubeck, Michael D., et al., "Topological Mapping of Antigenic Sites on the Influenza A/PR/8/34 Virus Hemagglutinin Using Monoclonal Antibodies", *Virology*, 113, (1981), 64-72.

Luytjes, W., "Amplification, Expression, and Packaging of a Foreign Gene by Influenza Virus", *Cell*, 59(6), (1989), 1107-1113.

MacAllister, DVM, C., et al., "OSU—Equine Vaccination Programs", Oklahoma Cooperative Extension Fact Sheet No. F-9119, (prior to Jan. 11, 2005), 4 pgs.

(56) References Cited

OTHER PUBLICATIONS

Mena, I., "Rescue of a Synthetic Choramphenicol Acetyltransferase RNA into influenza Virus-Like Particles obtained from recombinant plasmids", *Journal of Virology*, 70(8), (1996), 5016-5024.

Mumford, J. A., "OIE Standards", *Proceedings of the Fourth International Meeting of OIE and WHO Experts on Control of Equine Influenza*, (Havemeyer Foundation Monograph Series No. 7), Mumford, J. A., Editors, et al., R & W Publications Limited, (2003), 46-53.

Munoz, F. M., et al., "Current Research on Influenza and Other Respiratory Viruses: II International Symposium", *Antiviral Research*, 46(2), (May 2000), 91-124.

Nagai, Y., "Paramyxovirus Replication and Pathogenesis. Reverse Genetics Transforms Understanding", *Reviews in Medical Virology*, 9(2), (1999), 83-99.

Neumann, G., et al., "A Decade After the Generation of a Negative-Sense RNA Virus From Cloned cDNA—What Have We Learned?", *Journal of General Virology*, 83(11), (Nov. 2002), 2635-2662.

Neumann, G., et al., "Generation of influenza A viruses entirely from cloned cDNAs", *Proc. Natl. Acad. Sci. USA.*, 96(16), (1999), 9345-9350.

Neumann, G., et al., "Nuclear Import and Export of Influenza Virus Nucleoprotein", *Journal of Virology*, 71(12), (1997), 9690-9700.

Neumann, G., et al., "Reverse genetics of influenza virus.", *Virology*, 287(2), (Sep. 1, 2001), 243-50.

Neumann, G., et al., "RNA Polymerase I-Mediated Expression of Influenza Viral RNA Molecules", *Virology*, 202(1), (1994), 477-479.

Niwa, H., et al., "Efficient Selection for High-Expression Transfectants With a Novel Eukaryotic Factor", *Gene*, 108(2), (1991), 193-199.

Olsen, Christopher, et al., "Antigenic and genetic analysis of a recently isolated H1N1 swine influenze virus", *Am J Vet Res*, 54(10), (1993), 1630-1636.

Olsen, Christopher W., et al., "Immunogenicity and efficacy of baculovirus-expressed and DNA-based equine influenza virus hemagglutinin vaccines in mice", *Vaccine*, 15(10), (1997), 1149-1156.

Park, A. W., et al., "The Effects of Strain Heterology on the Epidemiology of Equine Influenza in a Vaccinated Population", *Proc. R. Soc. Lond. B.*, 271, (2004), 1547-1555.

Parks, C. L., et al., "Enhanced Measles Virus cDNA Rescue and Gene Expression After Heat Shock", *Journal of Virology*, 73(5), (May 1999), 3560-3566.

Peek, Simon F., et al., "Acute Respiratory Distress Syndrome and Fatal Interstitial Pneumonia Associated with Equine Influenza in a Neonatal Foal", *J Vet Intern Med*, vol. 18, (2004), 132-134.

Pekosz, A., "Commentary—Reverse Genetics of Negative-Strand RNA Viruses: Closing the Circle", *Proc. Natl. Acad. Sci. USA*, 96, (1999), 8804-8806.

Perez, D. R., et al., "The Matrix 1 Protein of Influenza A Virus Inhibits the Transcriptase Activity of a Model Influenza Reporter Genome in Vivo", *Virology*, 249(1), (1998), 52-61.

Pleschka, S., et al., "A Plasmid-Based Reverse Genetics System for Influenza A Virus", *Journal of Virology*, 70(6), (1996), 4188-4192.

Powell, D. W., "Overview of Equine Influenza From the American Perspective", Proceedings of the Fourth International Meeting of OIE and WHO Experts on Control of Equine Influenza, (Havemeyer Foundation Mongraph Series No. 7), Mumford, J. A., et al., Editors, R & W Publications Limited, (2003), 2-5.

Radecke, F., et al., "Rescue of Measles Viruses From Cloned DNA", *The EMBO Journal*, 14(23), (1995), 5773-5784.

Raymond, F. L., et al., "The Antigenicity and Evolution of Influenza H1 Haemagglutinin, from 1950-1957 and 1977-1983: Two Pathways from One Gene", *Virology*, 148, (1986), 275-287.

Roberts, A., et al., "Recovery of Negative-Strand RNA Virus from Plasmid DNAs: A Positive Approach Revitalizes a Negative Field", *Virology*, 247(1), (1998), 1-6.

Rose, J. K., "Positive Strands to the Rescue Again: A Segmented Negative-Strand RNA Virus Derived From Cloned cDNAs", *Proc. Natl. Acad. Sci. USA*, 93(26), (Dec. 24, 1996), 14998-15000.

Schnell, M. J., "Infectious Rabies Viruses From Cloned cDNA", *The EMBO Journal*, 13(18), (1994), 4195-4203.

Suzuki, Y., et al., "Origin and Evolution of Influenza Virus Hemagglutinin Genes", *Mol. Biol. Evol.*, 19(4), (2002), 501-509.

Townsend, H. G., et al., "Comparative Efficacy of Commercial Vaccines in Five Horses: Serologic Responses and Protection After Influenza Challenge", *Proceedings, 49th Annual Conference of the American Association of Equine Practitioners*, (2003), 3 pgs.

Wiley, D. C., et al., "Structural identification of the antibody-binding sites of Hong Kong influenza haemagglutinin and their involvement in antigenic variation", *Nature*, 289, (1981), 373-378.

Wiley, Don C., et al., "The Structiure and Function of the Hemagglutinin Membrane Glycoprotein of Influenza Virus", *Ann. Rev. Biochem.*, 56, (1987), 365-394.

Wilson, W. D., "Equine Influenza", *Vet. Clin. North Am. Equine Pract.*, 9(2), (Abstract Only), (1993), 257-282.

\* cited by examiner

HAamino

MKTTIILILLTHWAYSQNPISGNNTATLCLGHHAVANGTLVKTISDDQIEVTNATE
LVQSISMGKICNNSYRILDGRNCTLIDAMLGDPHCDAFQYENWDLFIERSSAFSN
CYPYDIPDYASLRSIVASSGTLEFTAEGFTWTGVTQNGRSGACKRGSADSFFSRL
NWLTKSGSSYPTLNVTMPNNKNFDKLYIWGIHHPSSNQEQTKLYIQESGRVTVST
KRSQQTIIPNIGSRPWVRGQSGRISIYWTIVKPGDILMINSNGNLVAPRGYFKLKT
GKSSVMRSDVPIDICVSECITPNGSISNDKPFQNVNKVTYGKCPKYIRQNTLKLAT
GMRNVPEKQIRGIFGAIAGFIENGWEGMVDGWYGFRYQNSEGTGQAADLKSTQ
AAIDQINGKLNRVIERTNEKFHQIEKEFSEVERRIQDLEKYVEDTKIDLWSYNAEL
LVALENQHTIDLTDAEMNKLFEKTRRQLRENAEDMGGGCFKIYHKCDNACIGSI
RNGTYDHYIYRDEALNNRFQIKGVELKSGYKDWILWISFAISCFLICVVLLGFIM
WACQKGNIRCNICI

SEQ ID NO:1

FIG. 1A

NAamino

MNPNQKIIAIGFASLGILIINVILHVVSIIVTVLVLNNNRTDLNCKGTIIREYNETVR
VEKITQWYNTSTIKYIERPSNEYYMNNTEPLCEAQGFAPFSKDNGIRIGSRGHVFV
IREPFVSCSPSECRTFFLTQGSLLNDKHSNGTVKDRSPYRTLMSVKIGQSPNVYQA
RFESVAWSATACHDGKKWMTVGVTGPDNQAIAVVNYGGVPVDIINSWAGDILR
TQESSCTCIKGDCYWVMTDGPANRQAKYRIFKAKDGRVIGQTDISFNGGHIEECS
CYPNEGKVECICRDNWTGTNRPILVISSDLSYTVGYLCAGIPTDTPRGEDSQFTGS
CTSPLGNKGYGVKGFGFRQGTDVWAGRTISRTSRSGFEIIKIRNGWTQNSKDQIR
RQVIIDDPNWSGYSGSFTLPVELTKKGCLVPCFWVEMIRGKPEETTIWTSSSSIVM
CGVDHKIASWSWHDGAILPFDIDKM

SEQ ID NO:2

FIG. 1B

PB1amino

MDVNPTLLFLKVPAQNAISTTFPYTGDPPYSHGTGTGYTMDTVNRTHQYSEKGK
WTTNTEIGAPQLNPIDGPLPEDNEPSGYAQTDCVLEAMAFLEESHPGIFENSCLET
MEVIQQTRVDKLTQGRQTYDWTLNRNQPAATALANTIEVFRSNGLTSNESGRLM
DFLKDVMESMNKEEMEITTHFQRKRRVRDNMTKRMVTQRTIGKKKQRLNRKS
YLIRTLTLNTMTKDAERGKLKRRAIATPGMQIRGFVYFVETLARRICEKLEQSGL
PVGGNEKKAKLANVVRKMMTNSQDTELSFTITGDNTKWNENQNPRIFLAMITYI
TRNQPEWFRNVLSIAPIMFSNKMARLGKGYMFESKSMKLRTQIPAGMLASIDLK
YFNDPTKKKIEKIRPLLVDGTASLSPGMMMGMFNMLSTVLGVSILNLGQRKYTK
TTYWWDGLQSSDDFALIVNAPNHEGIQAGVDRFYRTCKLVGINMSKKKSYINRT
GTFEFTSFFYRGFVANFSMELPSFGVSGINESADMSIGVTVIKNNMINNDLGPAT
AQMALQLFIKDYRYTYRCHRGDTQIQTRRSFELKKLWEQTRSKTGLLVSDGGPN
LYNIRNLHIPEVCLKWELMDEDYKGRLCNPLNPFVSHKEIESVNSAVVMPAHGP
AKSMEYDAVATTHSWIPKRNRSILNTSQRGILEDEQMYQKCCNLFEKFFPSSSYR
RPVGISSMVEAMVSRARIDARIDFESGRIKKDEFAEIMKICSTIEELRRQK

SEQ ID NO:3

FIG. 1C

PB2amino

MERIKELRDLMLQSRTREILTKTTVDHMAIIKKYTSGRQEKNPALRMKWMMAM
KYPITADKRIMEMIPERNEQGQTLWSKTNDAGSDRVMVSPLAVTWWNRNGPTT
STIHYPKVYKTYFEKVERLKHGTFGPVHFRNQVKIRRRVDVNPGHADLSAKEAQ
DVIMEVVFPNEVGARILTSESQLTITKEKKEELQDCKIAPLMVAYMLERELVRKT
RFLPVAGGTSSVYIEVLHLTQGTCWEQMYTPGGEVRNDDIDQSLIIAARNIVRRA
TVSADPLASLLEMCHSTQIGGIRMVDILKQNPTEEQAVDICKAAMGLRISSSFSFG
GFTFKRTSGSSVKREEEMLTGNLQTLKIRVHEGYEEFTMVGRRATAILRKATRRL
IQLIVSGRDEQSIAEAIIVAMVFSQEDCMIKAVRGDLNFVNRANQRLNPMHQLLR
HFQKDAKVLFQNWGIEPIDNVMGMIGILPDMTPSTEMSLRGVRVSKMGVDEYSS
TERVVVSIDRFLRVRDQRGNILLSPEEVSETQGTEKLTITYSSSMMWEINGPESVL
VNTYQWIIRNWEIVKIQWSQDPTMLYNKIEFEPFQSLVPRATRSQYSGFVRTLFQ
QMRDVLGTFDTAQIIKLLPFAAAPPEQSRMQFSSLTVNVRGSGMRILVRGNSPVF
NYNKATKRLTVLGKDAGALTEDPDEGTAGVESAVLRGFLILGKENKRYGPALSI
NELSKLAKGEKANVLIGQGDVVLVMKRKRDSSILTDSQTATKRIRMAIN

SEQ ID NO:4

FIG. 1D

PAamino

MEDFVRQCFNPMIVELAEKAMKEYGEDPKIETNKFAAICTHLEVCFMYSDFHFIN
ELSESVVIESGDPNALLKHRFEIIEGRDRTMAWTVVNSICNTTRAEKPKFLPDLYD
YKENRFVEIGVTRREVHIYYLEKANKIKSEKTHIHIFSFTGEEMATKADYTLDEES
RARIKTRLFTIRQEMASRGLWDSFRQSERGEETIEERFEITGTMRKLANYSLPPNF
SSLENFRVYVDGFEPNGCIESKLSQMSKEVNARIEPFSKTTPRPLKMPGGPPCHQR
SKFLLMDALKLSIEDPSHEGEGIPLYDAIKCMKTFFGWKEPSIVKPHEKGINPNYL
QTWKQVLAELQDLENEEKDPKTKNMKKTSQLKWALSENMAPEKVDFEDCKDIS
DLKQYDSDEPETRSLASWIQSEFNKACELTDSSWIELDEIGEDVAPIEYIASMRRN
YFTAEVSHCRATEYIMKGVYINTALLNASCAAMDEFQLIPMISKCRTKEGRRKTN
LYGFIVKGRSHLRNDTDVVNFVSMEFSLTDPRFEPHKWEKYCVLEIGDMLLRTA
VGQVSRPMFLYVRTNGTSKIKMKWGMEMRRCLLQSLQQIESMIEAESSVKEKD
MTKEFFENKSETWPIGESPKGVEEGSIGKVCRTLLAKSVFNSLYASPQLEGFSAES
RKLLLIVQALRDNLEPGTFDIGGLYESIEECLINDPWVLLNASWFNSFLTHALK

SEQ ID NO:5

FIG. 1E

NPamino

MASQGTKRSYEQMETDGERQNATEIRASVGRMVGGIGRFYVQMCTELKLNDHE
GRLIQNSITIERMVLSAFDERRNKYLEEHPSAGKDPKKTGGPIYRRKDGKWMREL
ILHDKEEIMRIWRQANNGEDATAGLTHMMIWHSNLNDTTYQRTRALVRTGMDP
RMCSLMQGSTLPRRSGAAGAAVKGVGTMVMELIRMIKRGINDRNFWRGENGR
RTRIAYERMCNILKGKFQTAAQRAMMDQVREGRNPGNAEIEDLIFLARSALILRG
SVAHKSCLPACVYGLAVTSGYDFEKEGYSLVGIDPFKLLQNSQIFSLIRPKENPAH
KSQLVWMACHSAAFEDLRVLNFIRGTKVIPRGQLTTRGVQIASNENMETIDSSTL
ELRSKYWAIRTRSGGNTSQQRASAGQISVQPTFSVQRNLPFERATIMAAFTGNTE
GRTSDMRTEIIRMMENAKSEDVSFQGRGVFELSDEKATNPIVPSFDMSNEGSYFF
GDNAEEFDS

SEQ ID NO:6

FIG. 1F

M1amino

MSLLTEVETYVLSIVPSGPLKAEIAQRLEDVFAGKNTDLEALMEWLKTRPILSPLT
KGILGFVFTLTVPSERGLQRRRFVQNALSGNGDPNNMDRAVKLYRKLKREITFH
GAKEVALSYSTGALASCMGLIYNRMGTVTTEVAFGLVCATCEQIADSQHRSHRQ
MVTTTNPLIRHENRMVLASTTAKAMEQMAGSSEQAAEAMEVASRARQMVQAM
RTIGTHPSSSAGLKDDLLENLQAYQKRMGVQMQRFK

SEQ ID NO:7

FIG. 1G

NS1amino

MDSNTVSSFQVDCFLWHVRKRFADQELGDAPFLDRLRRDQKSLRGRGSTLGLDI
ETATHAGKQIVEQILEKESDEALKMTIASVPTSRYLTDMTLDEMSRDWFMLMPK
QKVTGSLCIRMDQAIMDKNIILKANFSVIFERLETLILLRAFTEEGAVVGEISPLPSL
PGHTNEDVKNAIGVLIGGLKWNDNTVRISETLQRFAWRSSHENGRPSFPSKQKR
KMERTIKPKI

SEQ ID NO:8

TCATGAAGACAACCATTATTTTGATACTACTGACCCATTGGGCTTACAGTCAA
AACCCAATCAGTGGCAACAACACAGCCACATTGTGTCTGGGACACCATGCAG
TAGCAAATGGAACATTGGTAAAAACAATAAGTGATGATCAAATTGAGGTGAC
AAATGCTACAGAATTAGTTCAAAGCATTTCAATGGGGAAAATATGCAACAAC
TCATATAGAATTCTAGATGGAAGAAATTGCACATTAATAGATGCAATGCTAG
GAGACCCCCACTGTGACGCCTTTCAGTATGAGAATTGGGACCTCTTTATAGAA
AGAAGCAGCGCTTTCAGCAATTGCTACCCATATGACATCCCTGACTATGCATC
GCTCCGATCCATTGTAGCATCCTCAGGAACATTGGAATTCACAGCAGAGGGA
TTCACATGGACAGGTGTCACTCAAAACGGAAGAAGTGGAGCCTGCAAAAGG
GGATCAGCCGATAGTTTCTTTAGCCGACTGAATTGGCTAACAAAATCTGGAA
GCTCTTACCCCACATTGAATGTGACAATGCCTAACAATAAAAATTTCGACAA
GCTATACATCTGGGGGATTCATCACCCGAGCTCAAATCAAGAGCAGACAAAA
TTGTACATCCAAGAATCAGGACGAGTAACAGTCTCAACAAAAAGAAGTCAAC
AAACAATAATCCCTAACATCGGATCTAGACCGTGGGTCAGAGGTCAATCAGG
TAGGATAAGCATATACTGGACCATTGTAAAACCTGGAGATATCCTAATGATA
AACAGTAATGGCAACTTAGTTGCACCGCGGGGATATTTTAAATTGAAAACAG
GGAAAAGCTCTGTAATGAGATCAGATGTACCCATAGACATTTGTGTGTCTGA
ATGTATTACACCAAATGGAAGCATCTCCAACGACAAGCCATTCCAAAATGTG
AACAAAGTTACATATGGAAAATGCCCCAAGTATATCAGGCAAAACACTTTAA
AGCTGGCCACTGGGATGAGGAATGTACCAGAAAAGCAAATCAGAGGAATCT
TTGGAGCAATAGCGGGATTCATCGAAAACGGCTGGGAAGGAATGGTTGATGG
GTGGTATGGGTTCCGATATCAAAACTCTGAAGGAACAGGGCAAGCTGCAGAT
CTAAAGAGCACTCAAGCAGCCATCGACCAGATTAATGGAAAGTTAAACAGA
GTGATTGAAAGAACCAATGAGAAATTCCATCAAATAGAGAAGGAATTCTCAG
AAGTAGAAAGAAGAATTCAGGACTTGGAGAAATATGTAGAAGACACCAAAA
TAGACCTATGGTCCTACAATGCAGAATTGCTGGTGGCTCTAGAAAATCAACA
TACAATTGACTTAACAGATGCAGAAATGAATAAATTATTTGAGAAGACTAGA
CGCCAGTTAAGAGAAAACGCAGAAGACATGGGAGGTGGATGTTTCAAGATTT
ACCACAAATGTGATAATGCATGCATTGGATCAATAAGAAATGGACATATGA
CCATTACATATACAGAGATGAAGCATTAAACAACCGATTTCAGATCAAAGGT
GTAGAGTTGAAATCAGGCTACAAAGATTGGATACTGTGGATTTCATTCGCCA
TATCATGCTTCTTAATTTGCGTTGTTCTATTGGGTTTCATTATGTGGGCTTGCC
AAAAAGGCAACATCAGATGCAACATTTGCATTTGAG

SEQ ID NO:9

ATGAATCCAAATCAAAAGATAATAGCAATTGGATTTGCATCATTGGGGATAT
TAATCATTAATGTCATTCTCCATGTAGTCAGCATTATAGTAACAGTACTGGTC
CTCAATAACAATAGAACAGATCTGAACTGCAAAGGGACGATCATAAGAGAG
TACAATGAAACAGTAAGAGTAGAAAAAATTACTCAATGGTATAATACCAGTA
CAATTAAGTACATAGAGAGACCTTCAAATGAATACTACATGAACAACACTGA
ACCACTTTGTGAGGCCCAAGGCTTTGCACCATTTTCCAAAGATAATGGAATAC
GAATTGGGTCGAGAGGCCATGTTTTTGTGATAAGAGAACCTTTTGTATCATGT
TCGCCCTCAGAATGTAGAACCTTTTCCTCACACAGGGCTCATTACTCAATGA
CAAACATTCTAACGGCACAGTAAAGGACCGAAGTCCGTATAGGACTTTGATG
AGTGTCAAAATAGGGCAATCACCTAATGTATATCAAGCTAGGTTTGAATCGG
TGGCATGGTCAGCAACAGCATGCCATGATGGAAAAAAATGGATGACAGTTGG
AGTCACAGGGCCCGACAATCAAGCAATTGCAGTAGTGAACTATGGAGGTGTT
CCGGTTGATATTATTAATTCATGGGCAGGGGATATTTTAAGAACCCAAGAAT
CATCATGCACCTGCATTAAAGGAGACTGTTATTGGGTAATGACTGATGGACC
GGCAAATAGGCAAGCTAAATATAGGATATTCAAAGCAAAAGATGGAAGAGT
AATTGGACAGACTGATATAAGTTTCAATGGGGGACACATAGAGGAGTGTTCT
TGTTACCCCAATGAAGGGAAGGTGGAATGCATATGCAGGGACAATTGGACTG
GAACAAATAGACCAATTCTGGTAATATCTTCTGATCTATCGTACACAGTTGGA
TATTTGTGTGCTGGCATTCCCACTGACACTCCTAGGGGAGAGGATAGTCAATT
CACAGGCTCATGTACAAGTCCTTTGGGAAATAAAGGATACGGTGTAAAAGGT
TTCGGGTTTCGACAAGGAACTGACGTATGGGCCGGAAGGACAATTAGTAGGA
CTTCAAGATCAGGATTCGAAATAATAAAAATCAGGAATGGTTGGACACAGAA
CAGTAAAGACCAAATCAGGAGGCAAGTGATTATCGATGACCCAAATTGGTCA
GGATATAGCGGTTCTTTCACATTGCCGGTTGAACTAACAAAAAAGGGATGTT
TGGTCCCCTGTTTCTGGGTTGAAATGATTAGAGGTAAACCTGAAGAAACAAC
AATATGGACCTCTAGCAGCTCCATTGTGATGTGTGGAGTAGATCATAAAATT
GCCAGTTGGTCATGGCACGATGGAGCTATTCTTCCCTTTGACATCGATAAGAT
GTAA

SEQ ID NO:10

ATGGATGTCAATCCGACTCTACTTTTCTTAAAGGTGCCAGCGCAAAATGCTAT
AAGCACAACATTTCCTTATACTGGAGATCCTCCCTACAGTCATGGAACAGGG
ACAGGATACACCATGGATACTGTCAACAGAACACACCAATATTCAGAAAAAG
GGAAATGGACAACAAACACTGAGATTGGAGCACCACAACTTAATCCAATCGA
TGGACCACTTCCTGAAGACAATGAACCAAGTGGGTACGCCCAAACAGATTGT
GTATTGGAAGCAATGGCTTTCCTTGAAGAATCCCATCCCGGAATCTTTGAAAA
TTCGTGTCTTGAAACGATGGAGGTGATTCAGCAGACAAGAGTGGACAAACTA
ACACAAGGCCGACAAACTTATGATTGGACCTTGAATAGGAATCAACCTGCCG
CAACAGCACTTGCTAATACGATTGAAGTATTCAGATCAAATGGTCTGACTTCC
AATGAATCGGGGAGATTGATGGACTTCCTCAAAGATGTCATGGAGTCCATGA
ACAAGGAAGAAATGGAAATAACAACACACTTCCAACGGAAGAGAAGAGTAA
GAGACAACATGACAAAGAGAATGGTAACACAGAGAACCATAGGGAAGAAAA
AACAACGATTAAACAGAAAGAGCTATCTAATCAGAACATTAACCCTAAACAC
AATGACCAAGGACGCTGAGAGAGGGAAATTGAAACGACGAGCAATCGCTAC
CCCAGGGATGCAGATAAGAGGGTTTGTATATTTTGTTGAAACACTAGCCCGA
AGAATATGTGAAAAGCTTGAACAATCAGGATTGCCAGTTGGCGGTAATGAGA
AAAAGGCCAAACTGGCTAATGTCGTCAGAAAAATGATGACTAATTCCCAAGA
CACTGAACTCTCCTTCACCATCACTGGGGACAATACCAAATGGAATGAAAAT
CAGAACCCACGCATATTCCTGGCAATGATCACATACATAACTAGAAACCAGC
CAGAATGGTTCAGAAATGTTCTAAGCATTGCACCGATTATGTTCTCAAATAAA
ATGGCAAGACTGGGGAAAGGATATATGTTTGAAAGCAAAAGTATGAAATTG
AGAACTCAAATACCAGCAGGAATGCTTGCAAGCATTGACCTGAAATATTTCA
ATGATCCAACAAAAAAGAAAATTGAAAAGATACGACCACTTCTGGTTGACGG
GACTGCTTCACTGAGTCCTGGCATGATGATGGGAATGTTCAACATGTTGAGC
ACTGTGCTAGGTGTATCCATATTAAACCTGGGCCAGAGGAAATACACAAAGA
CCACATACTGGTGGGATGGTCTGCAATCATCCGATGACTTTGCTTTGATAGTG
AATGCGCCTAATCATGAAGGAATACAAGCTGGAGTAGACAGATTCTATAGGA
CTTGCAAACTGGTCGGGATCAACATGAGCAAAAGAAGTCCTACATAAATAG
AACTGGAACATTCGAATTCACAAGCTTTTTCTACCGGTATGGTTTTGTAGCCA
ATTTCAGCATGGAACTACCCAGTTTTGGGGTTTCCGGAATAAATGAATCTGCA
GACATGAGCATTGGAGTGACAGTCATCAAAAACAACATGATAAATAATGATC
TCGGTCCTGCCACGGCACAAATGGCACTCCAACTCTTCATTAAGGATTATCGG
TACACATACCGGTGCCATAGAGGTGATACCCAGATACAAACCAGAAGATCTT
TTGAGTTGAAGAAACTGTGGGAACAGACTCGATCAAAGACTGGTCTACTGGT
ATCAGATGGGGGTCCAAACCTATATAACATCAGAAACCTACACATCCCGGAA
GTCTGTTTAAAATGGGAGCTAATGGATGAAGATTATAAGGGGAGGCTATGCA
ATCCATTGAATCCTTTCGTTAGTCACAAAGAAATTGAATCAGTCAACAGTGCA
GTAGTAATGCCTGCGCATGGCCCTGCCAAAAGCATGGAGTATGATGCTGTTG
CAACAACACATTCTTGGATCCCCAAGAGGAACCGGTCCATATTGAACACAAG
CCAAAGGGGAATACTCGAAGATGAGCAGATGTATCAGAAATGCTGCAACCTG
TTTGAAAAATTCTTCCCCAGCAGCTCATACAGAAGACCAGTCGGGATTTCTAG
TATGGTTGAGGCCATGGTGTCCAGGGCCCGCATTGATGCACGAATTGACTTC
GAATCTGGACGGATAAAGAAGGATGAGTTCGCTGAGATCATGAAGATCTGTT
CCACCATTGAAGAGCTCAGACGGCAAAAATAGTGA

SEQ ID NO:11

ATGGAGAGAATAAAAGAACTGAGAGATCTGATGTTACAATCCCGCACCCGCG
AGATACTAACAAAAACTACTGTGGACCACATGGCCATAATCAAGAAATACAC
ATCAGGAAGACAAGAGAAGAACCCTGCACTTAGGATGAAATGGATGATGGC
AATGAAATACCCAATTACAGCAGATAAGAGGATAATGGAGATGATTCCTGAG
AGAAATGAACAGGGACAAACCCTTTGGAGCAAAACGAACGATGCTGGCTCA
GACCGCGTAATGGTATCACCTCTGGCAGTGACATGGTGGAATAGGAATGGAC
CAACAACAAGCACAATTCATTATCCAAAAGTCTACAAAACTTATTTTGAAAA
GGTTGAAAGATTGAAACACGGAACCTTTGGCCCCGTTCATTTTAGGAATCAA
GTCAAGATAAGACGAAGAGTTGATGTAAACCCTGGTCACGCGGACCTCAGTG
CCAAAGAAGCACAAGATGTGATCATGGAAGTTGTTTTCCCAAATGAAGTGGG
AGCCAGAATTCTAACATCGGAATCACAACTAACAATAACCAAAGAGAAAAA
GGAAGAACTTCAGGACTGCAAAATTGCTCCCTTGATGGTAGCATACATGCTA
GAAAGAGAGTTGGTCCGAAAACAAGGTTCCTCCCAGTAGCAGGCGGAACA
AGCAGTGTATACATTGAAGTGTTGCATCTGACTCAGGGAACATGCTGGGAGC
AAATGTACACCCCAGGAGGAGAAGTTAGAAACGATGATATTGATCAAAGTTT
AATTATTGCAGCCCGGAACATAGTGAGAAGAGCAACAGTATCAGCAGATCCA
CTAGCATCCCTACTGGAAATGTGCCACAGTACACAGATTGGTGGAATAAGGA
TGGTAGACATCCTTAAGCAGAATCCAACAGAGGAACAAGCTGTGGATATATG
CAAAGCAGCAATGGGATTGAGAATTAGCTCATCATTCAGCTTTGGTGGATTC
ACCTTCAAGAGAACAAGTGGATCATCAGTCAAGAGAGAAGAAGAAATGCTT
ACGGGCAACCTTCAAACATTGAAAATAAGAGTGCATGAGGGCTATGAAGAAT
TCACAATGGTCGGAAGAAGAGCAACAGCCATTCTCAGAAAGGCAACCAGAA
GATTGATTCAATTGATAGTAAGTGGGAGAGATGAACAGTCAATTGCTGAAGC
AATAATTGTAGCCATGGTGTTTTCGCAAGAAGATTGCATGATAAAAGCAGTT
CGAGGCGATTTGAACTTTGTTAATAGAGCAAATCAGCGCTTGAACCCCATGC
ATCAACTCTTGAGGCATTTCCAAAAGGATGCAAAAGTGCTTTTCCAAAATTG
GGGGATTGAACCCATCGACAATGTAATGGGAATGATTGGAATATTGCCTGAC
ATGACCCCAAGCACCGAGATGTCATTGAGAGGAGTGAGAGTCAGCAAAATG
GGAGTGGATGAGTACTCCAGCACTGAGAGAGTGGTGGTGAGCATTGACCGTT
TTTTAAGAGTTCGGGATCAAAGGGGAAACATACTACTGTCCCCTGAAGAAGT
CAGTGAAACACAAGGAACGGAAAAGCTGACAATAATTTATTCGTCATCAATG
ATGTGGGAGATTAATGGTCCCGAATCAGTGTTGGTCAATACTTATCAATGGAT
CATCAGGAACTGGGAAATTGTAAAAATTCAGTGGTCACAGGACCCCACAATG
TTATACAATAAGATAGAATTTGAGCCATTCCAATCCCTGGTCCCTAGGGCTAC
CAGAAGCCAATACAGCGGTTTCGTAAGAACCCTGTTTCAGCAAATGCGAGAT
GTACTTGGAACATTTGATACTGCTCAAATAATAAAACTCCTCCCTTTTGCCGC
TGCTCCTCCGGAACAGAGTAGGATGCAGTTCTCTTCTTTGACTGTTAATGTAA
GAGGTTCGGGAATGAGGATACTTGTAAGAGGCAATTCCCCAGTGTTCAACTA
CAATAAAGCCACTAAAAGGCTCACAGTCCTCGGAAAGGATGCAGGTGCGCTT
ACTGAGGACCCAGATGAAGGTACGGCTGGAGTAGAATCTGCTGTTCTAAGAG
GGTTTCTCATTTTAGGTAAAGAAAATAAGAGATATGGCCCAGCACTAAGCAT
CAATGAACTAAGCAAACTTGCAAAAGGGGAGAAGCCAATGTACTAATTGG
GCAAGGGGACGTAGTGTTGGTAATGAAACGGAAACGTGACTCTAGCATACTT
ACTGACAGCCAGACAGCGACCAAAAGGATTCGGATGGCCATCAATTAGT

SEQ ID NO:12

ATGGAAGACTTTGTGCGACAATGCTTCAATCCAATGATCGTCGAGCTTGCGG
AAAAGGCAATGAAAGAATATGGAGAGGACCCGAAAATCGAAACAAACAAAT
TTGCAGCAATATGCACTCACTTGGAAGTCTGCTTCATGTACTCGGATTTCCAC
TTTATTAATGAACTGAGTGAGTCAGTGGTCATAGAGTCTGGTGACCCAAATG
CTCTTTTGAAACACAGATTTGAAATCATTGAGGGGAGAGATCGAACAATGGC
ATGGACAGTAGTAAACAGCATCTGCAACACCACAAGAGCTGAAAAACCTAA
ATTTCTTCCAGATTTATACGACTATAAGGAGAACAGATTTGTTGAAATTGGTG
TGACAAGGAGAGAAGTTCACATATACTACCTGGAGAAGGCCAACAAAATAA
AGTCTGAGAAAACACATATCCACATTTTCTCATTTACAGGAGAGGAAATGGC
TACAAAAGCGGACTATACTCTTGATGAAGAGTAGAGCCAGGATCAAGACC
AGACTATTCACTATAAGACAAGAAATGGCCAGTAGAGGCCTCTGGGATTCCT
TTCGTCAGTCCGAGAGAGGCGAAGAGACAATTGAAGAAAGATTTGAAATCAC
AGGGACGATGCGCAAGCTTGCCAATTACAGTCTCCCACCGAACTTCTCCAGC
CTTGAAAATTTTAGAGTCTATGTGGATGGATTCGAACCGAACGGCTGCATTG
AGAGTAAGCTTTCTCAAATGTCCAAAGAAGTAAATGCCAGAATCGAACCATT
TTCAAAGACAACACCCCGACCACTCAAAATGCCAGGTGGTCCACCCTGCCAT
CAGCGATCTAAATTCCTGCTAATGGATGCTCTGAAACTGAGCATTGAGGACC
CAAGTCACGAGGGAGAGGGAATACCACTATATGATGCCATCAAATGCATGAA
AACTTTCTTTGGATGGAAGAGCCCAGTATTGTTAAACCACATGAAAAGGGT
ATAAACCCGAACTATCTCCAAACTTGGAAGCAAGTATTAGCAGAATTACAAG
ACCTTGAGAACGAAGAAAAGGACCCCAAGACCAAGAATATGAAAAAAACAA
GCCAATTGAAATGGGCACTTAGTGAAAATATGGCACCAGAGAAAGTGGATTT
TGAGGATTGTAAAGACATCAGTGATTTAAAACAGTATGACAGTGATGAGCCA
GAAACAAGGTCTCTTGCAAGTTGGATTCAAAGTGAGTTCAACAAAGCTTGTG
AACTGACAGATTCAAGCTGGATAGAGCTCGATGAAATTGGGGAGGATGTTGC
CCCAATAGAATACATTGCGAGCATGAGGAGAAATTATTTTACTGCTGAGGTT
TCCCATTGTAGAGCAACAGAATATATAATGAAGGGAGTGTACATCAACACTG
CTCTACTCAATGCATCCTGTGCTGCGATGGATGAATTCCAATTAATTCCGATG
ATAAGTAAATGCAGGACCAAAGAAGGGAGAAGGAAGACAAATTTATATGGA
TTCATAGTAAAGGGAAGGTCCCATTTAAGAAATGATACTGACGTGGTGAACT
TTGTAAGTATGGAATTTTCTCTCACTGATCCAAGATTTGAGCCACACAAATGG
GAAAAATACTGCGTTCTAGAAATTGGAGACATGCTTCTAAGAACTGCTGTAG
GTCAAGTGTCAAGACCCATGTTTTTGTATGTAAGGACAAATGGAACCTCTAA
AATTAAAATGAAATGGGGAATGGAAATGAGGCGCTGCCTCCTTCAGTCTCTG
CAACAGATTGAAAGCATGATCGAAGCTGAGTCCTCAGTCAAAGAAAAGGAC
ATGACCAAAGAATTTTTTGAGAACAAATCAGAGACATGGCCTATAGGAGAGT
CCCCCAAAGGAGTGGAAGAGGGCTCAATCGGGAAGGTTTGCAGGACCTTATT
AGCAAAATCTGTGTTTAACAGTTTGTATGCATCTCCACAACTGGAAGGGTTTT
CAGCTGAATCTAGGAAATTACTTCTCATTGTTCAGGCTCTTAGGGATAACCTG
GAACCTGGAACCTTTGATATTGGGGGGTTATATGAATCAATTGAGGAGTGCC
TGATTAATGATCCCTGGGTTTTGCTTAATGCATCTTGGTTCAACTCCTTCCTTA
CACATGCACTGAAGTAGTTGTGGCAATGCTACTATTTGCTATCCATACTGTCC
AAAAAAGTACCTTGTTTCTACT

SEQ ID NO:13

```
ATGGCGTCTCAAGGCACCAAACGATCCTATGAACAGATGGAAACTGATGGGG
AACGCCAGAATGCAACTGAAATCAGAGCATCTGTCGGAAGGATGGTGGGAG
GAATCGGCCGGTTTTATGTTCAGATGTGTACTGAGCTTAAACTAAACGACCAT
GAAGGGCGGCTGATTCAGAACAGCATAACAATAGAAAGGATGGTACTTTCGG
CATTCGACGAAAGAAGAAACAAGTATCTCGAGGAGCATCCCAGTGCTGGGA
AAGACCCTAAGAAAACAGGAGGCCCGATATACAGAAGGAAAGATGGGAAAT
GGATGAGGGAACTCATCCTCCATGATAAAGAAGAAATCATGAGAATCTGGCG
TCAGGCCAACAATGGTGAAGACGCTACTGCTGGTCTTACTCATATGATGATCT
GGCACTCCAATCTCAATGACACCACATACCAAAGAACAAGGGCTCTTGTTCG
GACTGGGATGGATCCCAGAATGTGCTCTCTGATGCAAGGCTCAACCCTCCCA
CGGAGATCTGGAGCCGCTGGTGCTGCAGTAAAAGGTGTTGGAACAATGGTAA
TGGAACTCATCAGAATGATCAAACGCGGAATAAATGATCGGAATTTCTGGAG
AGGTGAAAATGGTCGAAGAACCAGAATTGCTTATGAAAGAATGTGCAATATC
CTCAAAGGGAAATTTCAGACAGCAGCACAACGGGCTATGATGGACCAGGTG
AGGGAAGGCCGCAATCCTGGAAACGCTGAGATTGAGGATCTCATTTTCTTGG
CACGATCAGCACTTATTTTGAGAGGATCAGTAGCCCATAAATCATGCCTACCT
GCCTGTGTTTATGGCCTTGCAGTAACCAGTGGGTATGACTTTGAGAAGGAAG
GATACTCTCTGGTTGGAATTGATCCTTTCAAACTACTCCAGAACAGTCAAATT
TTCAGTCTAATCAGACCAAAAGAAAACCCAGCACACAAGAGCCAGTTGGTGT
GGATGGCATGCCATTCTGCAGCATTTGAGGACCTGAGAGTTTTAAATTTCATT
AGAGGAACCAAAGTAATCCCAAGAGGACAGTTAACAACCAGAGGAGTTCAA
ATAGCTTCAAATGAAAACATGGAGACAATAGATTCTAGCACACTTGAACTGA
GAAGCAAATATTGGGCAATAAGGACCAGAAGCGGAGGAAACACCAGTCAAC
AGAGAGCATCTGCAGGACAGATAAGTGTGCAACCTACTTTCTCAGTACAGAG
AAATCTTCCCTTTGAGAGAGCAACCATTATGGCTGCATTCACTGGTAACACTG
AAGGGAGGACTTCCGACATGAGAACGGAAATCATAAGGATGATGGAAAATG
CCAAATCAGAAGATGTGTCTTTCCAGGGGCGGGGAGTCTTCGAGCTCTCGGA
CGAAAAGGCAACGAACCCGATCGTGCCTTCCTTTGACATGAGCAATGAAGGG
TCTTATTTCTTCGGAGACAATGCTGAGGAGTTTGACAGTTAAA
```

SEQ ID NO:14

ATGAGTCTTCTAACCGAGGTCGAAACGTACGTTCTCTCTATCGTACCATCAGG
CCCCCTCAAAGCCGAGATCGCGCAGAGACTTGAAGATGTCTTTGCAGGGAAG
AACACCGATCTTGAGGCACTCATGGAATGGCTAAAGACAAGACCAATCCTGT
CACCTCTGACTAAAGGGATTTTAGGATTTGTATTCACGCTCACCGTGCCCAGT
GAGCGAGGACTGCAGCGTAGACGCTTTGTCCAAAATGCCCTTAGTGGAAACG
GAGATCCAAACAACATGGACAGAGCAGTAAAACTGTACAGGAAGCTTAAAA
GAGAAATAACATTCCATGGGGCAAAAGAGGTGGCACTCAGCTATTCCACTGG
TGCACTAGCCAGCTGCATGGGACTCATATACAACAGAATGGGAACTGTTACA
ACCGAAGTGGCATTTGGCCTGGTATGCGCCACATGTGAACAGATTGCTGATT
CCCAGCATCGGTCTCACAGGCAGATGGTGACAACAACCAACCCATTAATCAG
ACATGAAAACAGAATGGTATTAGCCAGTACCACGGCTAAAGCCATGGAACA
GATGGCAGGATCGAGTGAGCAGGCAGCAGAGGCCATGGAGGTTGCTAGTAG
GGCTAGGCAGATGGTACAGGCAATGAGAACCATTGGGACCCACCCTAGCTCC
AGTGCCGGTTTGAAAGATGATCTCCTTGAAAATTTACAGGCCTACCAGAAAC
GGATGGGAGTGCAAATGCAGCGATTCAAGTGATCCTCTCGTTATTGCAGCAA
GTATCATTGGGATCTTGCACTTGATATTGTGGATTCTTGATCGTCTTTTCTTCA
AATTCATTTATCGTCGCCTTAAATACGGGTTGAAAAGAGGGCCTTCTACGGA
AGGAGTACCTGAGTCTATGAGGGAAGAATATCGGCAGGAACAGCAGAATGC
TGTGGATGTTGACGATGGTCATTTTGTCAACATAGAGCTGGAGTAA

SEQ ID NO:15

ATGGATTCCAACACTGTGTCAAGCTTTCAGGTAGACTGTTTTCTTTGGCATGT
CCGCAAACGATTCGCAGACCAAGAACTGGGTGATGCCCCATTCCTTGACCGG
CTTCGCCGAGACCAGAAGTCCCTAAGGGGAAGAGGTAGCACTCTTGGTCTGG
ACATCGAAACAGCCACTCATGCAGGAAAGCAGATAGTGGAGCAGATTCTGG
AAAAGGAATCAGATGAGGCACTTAAAATGACCATTGCCTCTGTTCCTACTTC
ACGCTACTTAACTGACATGACTCTTGATGAGATGTCAAGAGACTGGTTCATGC
TCATGCCCAAGCAAAAAGTAACAGGCTCCCTATGTATAAGAATGGACCAGGC
AATCATGGATAAGAACATCATACTTAAAGCAAACTTTAGTGTGATTTTCGAA
AGGCTGGAAACACTAATACTACTTAGAGCCTTCACCGAAGAAGGAGCAGTCG
TTGGCGAAATTTCACCATTACCTTCTCTTCCAGGACATACTAATGAGGATGTC
AAAAATGCAATTGGGGTCCTCATCGGAGGACTTAAATGGAATGATAATACGG
TTAGAATCTCTGAAACTCTACAGAGATTCGCTTGGAGAAGCAGTCATGAGAA
TGGGAGACCTTCATTCCCTTCAAAGCAGAAACGAAAAATGGAGAGAACAATT
AAGCCAAAAATTTGAAGAAATAAGATGGTTGATTGAAGAAGTGCGACATAG
ATTGAAAAATACAGAAAATAGTTTTGAACAAATAACATTTATGCAAGCCTTA
CAACTATTGCTTGAAGTAGAACAAGAGATAAGAACTTTCTCGTTTCAGCTTAT
TTAA

SEQ ID NO:16

FIG. 1P

M2amino

MSLLTEVETPTRNGWECKCSDSSDPLVIAASIIGILHLILWILDRLFFKFIYRRLKY
GLKRGPSTEGVPESMREEYRQEQQNAVDVDDGHFVNIELE

SEQ ID NO:17

FIG. 1Q

NS2amino

MDSNTVSSFQLMRMSKMQLGSSSEDLNGMIIRLESLKLYRDSLGEAVMRMGDL
HSLQSRNEKWREQLSQKFEEIRWLIEEVRHRLKNTENSFEQITFMQALQLLLEVE
QEIRTFSFQLI

SEQ ID NO:18

FIG. 1R

| | |
|---|---|
| M K T T I I L I L L T H W A Y S Q N P I S G N N T A T L C L | A/Equine/WI/1/03 |
| M K T T I I L I L L T H W A Y S Q N P I S G N N T A T L C L | A/Equine/New York/99 |
| G H H A V A N G T L V K T I S D D Q I E V T N A T E L V Q S | A/Equine/WI/1/03 |
| G H H A V A N G T L V K T I S D D Q I E V T N A T E L V Q S | A/Equine/New York/99 |
| I S M

SEQUENCE LISTING

```
<160> NUMBER OF SEQ ID NOS: 20

<210> SEQ ID NO 1
<211> LENGTH: 565
<212> TYPE: PRT
<213> ORGANISM: Influenza A Virus

<400> SEQUENCE: 1

Met Lys Thr Thr Ile Ile Leu Ile Leu Leu Thr His Trp Ala Tyr Ser
1               5                   10                  15

Gln Asn Pro Ile Ser Gly Asn Asn Thr Ala Thr Leu Cys Leu Gly His
            20                  25                  30

His Ala Val Ala Asn Gly Thr Leu Val Lys Thr Ile Ser Asp Asp Gln
        35                  40                  45

Ile Glu Val Thr Asn Ala Thr Glu Leu Val Gln Ser Ile Ser Met Gly
    50                  55                  60

Lys Ile Cys Asn Asn Ser Tyr Arg Ile Leu Asp Gly Arg Asn Cys Thr
65                  70                  75                  80

Leu Ile Asp Ala Met Leu Gly Asp Pro His Cys Asp Ala Phe Gln Tyr
                85                  90                  95

Glu Asn Trp Asp Leu Phe Ile Glu Arg Ser Ser Ala Phe Ser Asn Cys
            100                 105                 110

Tyr Pro Tyr Asp Ile Pro Asp Tyr Ala Ser Leu Arg Ser Ile Val Ala
        115                 120                 125

Ser Ser Gly Thr Leu Glu Phe Thr Ala Glu Gly Phe Thr Trp Thr Gly
    130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175
```

-continued

Pro Thr Leu Asn Val Thr Met Pro Asn Asn Lys Asn Phe Asp Lys Leu
            180                 185                 190

Tyr Ile Trp Gly Ile His His Pro Ser Ser Asn Gln Glu Gln Thr Lys
        195                 200                 205

Leu Tyr Ile Gln Glu Ser Gly Arg Val Thr Val Ser Thr Lys Arg Ser
    210                 215                 220

Gln Gln Thr Ile Ile Pro Asn Ile Gly Ser Arg Pro Trp Val Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
            260                 265                 270

Phe Lys Leu Lys Thr Gly Lys Ser Ser Val Met Arg Ser Asp Val Pro
        275                 280                 285

Ile Asp Ile Cys Val Ser Glu Cys Ile Thr Pro Asn Gly Ser Ile Ser
    290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Ile Arg Gly Ile Phe Gly Ala Ile Ala Gly
            340                 345                 350

Phe Ile Glu Asn Gly Trp Glu Gly Met Val Asp Gly Trp Tyr Gly Phe
        355                 360                 365

Arg Tyr Gln Asn Ser Glu Gly Thr Gly Gln Ala Ala Asp Leu Lys Ser
    370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                405                 410                 415

Val Glu Arg Arg Ile Gln Asp Leu Glu Lys Tyr Val Glu Asp Thr Lys
            420                 425                 430

Ile Asp Leu Trp Ser Tyr Asn Ala Glu Leu Leu Val Ala Leu Glu Asn
        435                 440                 445

Gln His Thr Ile Asp Leu Thr Asp Ala Glu Met Asn Lys Leu Phe Glu
    450                 455                 460

Lys Thr Arg Arg Gln Leu Arg Glu Asn Ala Glu Asp Met Gly Gly Gly
465                 470                 475                 480

Cys Phe Lys Ile Tyr His Lys Cys Asp Asn Ala Cys Ile Gly Ser Ile
                485                 490                 495

Arg Asn Gly Thr Tyr Asp His Tyr Ile Tyr Arg Asp Glu Ala Leu Asn
            500                 505                 510

Asn Arg Phe Gln Ile Lys Gly Val Glu Leu Lys Ser Gly Tyr Lys Asp
        515                 520                 525

Trp Ile Leu Trp Ile Ser Phe Ala Ile Ser Cys Phe Leu Ile Cys Val
    530                 535                 540

Val Leu Leu Gly Phe Ile Met Trp Ala Cys Gln Lys Gly Asn Ile Arg
545                 550                 555                 560

Cys Asn Ile Cys Ile
                565

<210> SEQ ID NO 2
<211> LENGTH: 470
<212> TYPE: PRT

<213> ORGANISM: Influenza A Virus

<400> SEQUENCE: 2

```
Met Asn Pro Asn Gln Lys Ile Ile Ala Ile Gly Phe Ala Ser Leu Gly
  1               5                  10                  15
Ile Leu Ile Ile Asn Val Ile Leu His Val Val Ser Ile Ile Val Thr
             20                  25                  30
Val Leu Val Leu Asn Asn Asn Arg Thr Asp Leu Asn Cys Lys Gly Thr
         35                  40                  45
Ile Ile Arg Glu Tyr Asn Glu Thr Val Arg Val Glu Lys Ile Thr Gln
 50                  55                  60
Trp Tyr Asn Thr Ser Thr Ile Lys Tyr Ile Glu Arg Pro Ser Asn Glu
 65                  70                  75                  80
Tyr Tyr Met Asn Asn Thr Glu Pro Leu Cys Glu Ala Gln Gly Phe Ala
                 85                  90                  95
Pro Phe Ser Lys Asp Asn Gly Ile Arg Ile Gly Ser Arg Gly His Val
            100                 105                 110
Phe Val Ile Arg Glu Pro Phe Val Ser Cys Ser Pro Ser Glu Cys Arg
        115                 120                 125
Thr Phe Phe Leu Thr Gln Gly Ser Leu Leu Asn Asp Lys His Ser Asn
130                 135                 140
Gly Thr Val Lys Asp Arg Ser Pro Tyr Arg Thr Leu Met Ser Val Lys
145                 150                 155                 160
Ile Gly Gln Ser Pro Asn Val Tyr Gln Ala Arg Phe Glu Ser Val Ala
                165                 170                 175
Trp Ser Ala Thr Ala Cys His Asp Gly Lys Lys Trp Met Thr Val Gly
            180                 185                 190
Val Thr Gly Pro Asp Asn Gln Ala Ile Ala Val Val Asn Tyr Gly Gly
        195                 200                 205
Val Pro Val Asp Ile Ile Asn Ser Trp Ala Gly Asp Ile Leu Arg Thr
210                 215                 220
Gln Glu Ser Ser Cys Thr Cys Ile Lys Gly Asp Cys Tyr Trp Val Met
225                 230                 235                 240
Thr Asp Gly Pro Ala Asn Arg Gln Ala Lys Tyr Arg Ile Phe Lys Ala
                245                 250                 255
Lys Asp Gly Arg Val Ile Gly Gln Thr Asp Ile Ser Phe Asn Gly Gly
            260                 265                 270
His Ile Glu Glu Cys Ser Cys Tyr Pro Asn Glu Gly Lys Val Glu Cys
        275                 280                 285
Ile Cys Arg Asp Asn Trp Thr Gly Thr Asn Arg Pro Ile Leu Val Ile
290                 295                 300
Ser Ser Asp Leu Ser Tyr Thr Val Gly Tyr Leu Cys Ala Gly Ile Pro
305                 310                 315                 320
Thr Asp Thr Pro Arg Gly Glu Asp Ser Gln Phe Thr Gly Ser Cys Thr
                325                 330                 335
Ser Pro Leu Gly Asn Lys Gly Tyr Gly Val Lys Gly Phe Gly Phe Arg
            340                 345                 350
Gln Gly Thr Asp Val Trp Ala Gly Arg Thr Ile Ser Arg Thr Ser Arg
        355                 360                 365
Ser Gly Phe Glu Ile Ile Lys Ile Arg Asn Gly Trp Thr Gln Asn Ser
370                 375                 380
Lys Asp Gln Ile Arg Arg Gln Val Ile Ile Asp Asp Pro Asn Trp Ser
385                 390                 395                 400
```

-continued

```
Gly Tyr Ser Gly Ser Phe Thr Leu Pro Val Glu Leu Thr Lys Lys Gly
                405                 410                 415

Cys Leu Val Pro Cys Phe Trp Val Glu Met Ile Arg Gly Lys Pro Glu
            420                 425                 430

Glu Thr Thr Ile Trp Thr Ser Ser Ser Ser Ile Val Met Cys Gly Val
        435                 440                 445

Asp His Lys Ile Ala Ser Trp Ser Trp His Asp Gly Ala Ile Leu Pro
    450                 455                 460

Phe Asp Ile Asp Lys Met
465                 470

<210> SEQ ID NO 3
<211> LENGTH: 757
<212> TYPE: PRT
<213> ORGANISM: Influenza A Virus

<400> SEQUENCE: 3

Met Asp Val Asn Pro Thr Leu Leu Phe Leu Lys Val Pro Ala Gln Asn
 1               5                  10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Ile Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ser Asn Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
        195                 200                 205

Lys Gln Arg Leu Asn Arg Lys Ser Tyr Leu Ile Arg Thr Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

```
Asp Asn Thr Lys Trp Asn Glu Asn Gln Asn Pro Arg Ile Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
                355                 360                 365

Pro Ala Gly Met Leu Ala Ser Ile Asp Leu Lys Tyr Phe Asn Asp Pro
370                 375                 380

Thr Lys Lys Lys Ile Glu Lys Ile Arg Pro Leu Leu Val Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Arg Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
                500                 505                 510

Gly Val Ser Gly Ile Asn Glu Ser Ala Asp Met Ser Ile Gly Val Thr
            515                 520                 525

Val Ile Lys Asn Asn Met Ile Asn Asn Asp Leu Gly Pro Ala Thr Ala
530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Thr Gly Leu Leu Val Ser
                580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Lys Gly Arg Leu
            610                 615                 620

Cys Asn Pro Leu Asn Pro Phe Val Ser His Lys Glu Ile Glu Ser Val
625                 630                 635                 640

Asn Ser Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
                660                 665                 670

Ser Ile Leu Asn Thr Ser Gln Arg Gly Ile Leu Glu Asp Glu Gln Met
            675                 680                 685

Tyr Gln Lys Cys Cys Asn Leu Phe Glu Lys Phe Phe Pro Ser Ser Ser
        690                 695                 700

Tyr Arg Arg Pro Val Gly Ile Ser Ser Met Val Glu Ala Met Val Ser
705                 710                 715                 720
```

```
Arg Ala Arg Ile Asp Ala Arg Ile Asp Phe Glu Ser Gly Arg Ile Lys
                725                 730                 735

Lys Asp Glu Phe Ala Glu Ile Met Lys Ile Cys Ser Thr Ile Glu Glu
            740                 745                 750

Leu Arg Arg Gln Lys
        755

<210> SEQ ID NO 4
<211> LENGTH: 759
<212> TYPE: PRT
<213> ORGANISM: Influenza A Virus

<400> SEQUENCE: 4

Met Glu Arg Ile Lys Glu Leu Arg Asp Leu Met Leu Gln Ser Arg Thr
  1               5                  10                  15

Arg Glu Ile Leu Thr Lys Thr Thr Val Asp His Met Ala Ile Ile Lys
             20                  25                  30

Lys Tyr Thr Ser Gly Arg Gln Glu Lys Asn Pro Ala Leu Arg Met Lys
         35                  40                  45

Trp Met Met Ala Met Lys Tyr Pro Ile Thr Ala Asp Lys Arg Ile Met
     50                  55                  60

Glu Met Ile Pro Glu Arg Asn Glu Gln Gly Gln Thr Leu Trp Ser Lys
 65                  70                  75                  80

Thr Asn Asp Ala Gly Ser Asp Arg Val Met Val Ser Pro Leu Ala Val
                 85                  90                  95

Thr Trp Trp Asn Arg Asn Gly Pro Thr Thr Ser Thr Ile His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335
```

-continued

```
Ser Val Lys Arg Glu Glu Met Leu Thr Gly Asn Leu Gln Thr Leu
            340                 345                 350
Lys Ile Arg Val His Glu Gly Tyr Glu Glu Phe Thr Met Val Gly Arg
            355                 360                 365
Arg Ala Thr Ala Ile Leu Arg Lys Ala Thr Arg Leu Ile Gln Leu
            370                 375                 380
Ile Val Ser Gly Arg Asp Glu Gln Ser Ile Ala Glu Ala Ile Val
385                 390                 395                 400
Ala Met Val Phe Ser Gln Glu Asp Cys Met Ile Lys Ala Val Arg Gly
                405                 410                 415
Asp Leu Asn Phe Val Asn Arg Ala Asn Gln Arg Leu Asn Pro Met His
                420                 425                 430
Gln Leu Leu Arg His Phe Gln Lys Asp Ala Lys Val Leu Phe Gln Asn
            435                 440                 445
Trp Gly Ile Glu Pro Ile Asp Asn Val Met Gly Met Ile Gly Ile Leu
            450                 455                 460
Pro Asp Met Thr Pro Ser Thr Glu Met Ser Leu Arg Gly Val Arg Val
465                 470                 475                 480
Ser Lys Met Gly Val Asp Glu Tyr Ser Ser Thr Glu Arg Val Val Val
                485                 490                 495
Ser Ile Asp Arg Phe Leu Arg Val Arg Asp Gln Arg Gly Asn Ile Leu
                500                 505                 510
Leu Ser Pro Glu Glu Val Ser Glu Thr Gln Gly Thr Glu Lys Leu Thr
            515                 520                 525
Ile Ile Tyr Ser Ser Met Met Trp Glu Ile Asn Gly Pro Glu Ser
            530                 535                 540
Val Leu Val Asn Thr Tyr Gln Trp Ile Ile Arg Asn Trp Glu Ile Val
545                 550                 555                 560
Lys Ile Gln Trp Ser Gln Asp Pro Thr Met Leu Tyr Asn Lys Ile Glu
                565                 570                 575
Phe Glu Pro Phe Gln Ser Leu Val Pro Arg Ala Thr Arg Ser Gln Tyr
                580                 585                 590
Ser Gly Phe Val Arg Thr Leu Phe Gln Gln Met Arg Asp Val Leu Gly
            595                 600                 605
Thr Phe Asp Thr Ala Gln Ile Ile Lys Leu Leu Pro Phe Ala Ala Ala
            610                 615                 620
Pro Pro Glu Gln Ser Arg Met Gln Phe Ser Ser Leu Thr Val Asn Val
625                 630                 635                 640
Arg Gly Ser Gly Met Arg Ile Leu Val Arg Gly Asn Ser Pro Val Phe
                645                 650                 655
Asn Tyr Asn Lys Ala Thr Lys Arg Leu Thr Val Leu Gly Lys Asp Ala
                660                 665                 670
Gly Ala Leu Thr Glu Asp Pro Asp Glu Gly Thr Ala Gly Val Glu Ser
            675                 680                 685
Ala Val Leu Arg Gly Phe Leu Ile Leu Gly Lys Glu Asn Lys Arg Tyr
            690                 695                 700
Gly Pro Ala Leu Ser Ile Asn Glu Leu Ser Lys Leu Ala Lys Gly Glu
705                 710                 715                 720
Lys Ala Asn Val Leu Ile Gly Gln Gly Asp Val Val Leu Val Met Lys
                725                 730                 735
Arg Lys Arg Asp Ser Ser Ile Leu Thr Asp Ser Gln Thr Ala Thr Lys
            740                 745                 750
```

```
Arg Ile Arg Met Ala Ile Asn
            755

<210> SEQ ID NO 5
<211> LENGTH: 716
<212> TYPE: PRT
<213> ORGANISM: Influenza A Virus

<400> SEQUENCE: 5

Met Glu Asp Phe Val Arg Gln Cys Phe Asn Pro Met Ile Val Glu Leu
 1               5                  10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Leu Ser Glu Ser Val Val Ile Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Arg Ala Glu Lys Pro Lys Phe Leu Pro Asp Leu Tyr Asp Tyr
            100                 105                 110

Lys Glu Asn Arg Phe Val Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asn Tyr Ser Leu Pro Pro Asn Phe Ser
    210                 215                 220

Ser Leu Glu Asn Phe Arg Val Tyr Val Asp Gly Phe Glu Pro Asn Gly
225                 230                 235                 240

Cys Ile Glu Ser Lys Leu Ser Gln Met Ser Lys Glu Val Asn Ala Arg
                245                 250                 255

Ile Glu Pro Phe Ser Lys Thr Thr Pro Arg Pro Leu Lys Met Pro Gly
            260                 265                 270

Gly Pro Pro Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Ser Ile Val Lys Pro His Glu Lys Gly Ile Asn Pro Asn Tyr Leu Gln
                325                 330                 335

Thr Trp Lys Gln Val Leu Ala Glu Leu Gln Asp Leu Glu Asn Glu Glu
            340                 345                 350

Lys Asp Pro Lys Thr Lys Asn Met Lys Lys Thr Ser Gln Leu Lys Trp
        355                 360                 365
```

Ala Leu Ser Glu Asn Met Ala Pro Glu Lys Val Asp Phe Glu Asp Cys
        370                 375                 380

Lys Asp Ile Ser Asp Leu Lys Gln Tyr Asp Ser Asp Glu Pro Glu Thr
385                 390                 395                 400

Arg Ser Leu Ala Ser Trp Ile Gln Ser Glu Phe Asn Lys Ala Cys Glu
            405                 410                 415

Leu Thr Asp Ser Ser Trp Ile Glu Leu Asp Glu Ile Gly Glu Asp Val
        420                 425                 430

Ala Pro Ile Glu Tyr Ile Ala Ser Met Arg Arg Asn Tyr Phe Thr Ala
            435                 440                 445

Glu Val Ser His Cys Arg Ala Thr Glu Tyr Ile Met Lys Gly Val Tyr
        450                 455                 460

Ile Asn Thr Ala Leu Leu Asn Ala Ser Cys Ala Ala Met Asp Glu Phe
465                 470                 475                 480

Gln Leu Ile Pro Met Ile Ser Lys Cys Arg Thr Lys Glu Gly Arg Arg
            485                 490                 495

Lys Thr Asn Leu Tyr Gly Phe Ile Val Lys Gly Arg Ser His Leu Arg
        500                 505                 510

Asn Asp Thr Asp Val Val Asn Phe Val Ser Met Glu Phe Ser Leu Thr
        515                 520                 525

Asp Pro Arg Phe Glu Pro His Lys Trp Glu Lys Tyr Cys Val Leu Glu
        530                 535                 540

Ile Gly Asp Met Leu Leu Arg Thr Ala Val Gly Gln Val Ser Arg Pro
545                 550                 555                 560

Met Phe Leu Tyr Val Arg Thr Asn Gly Thr Ser Lys Ile Lys Met Lys
            565                 570                 575

Trp Gly Met Glu Met Arg Arg Cys Leu Leu Gln Ser Leu Gln Gln Ile
        580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
        610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
            645                 650                 655

Gly Phe Ser Ala Glu Ser Arg Lys Leu Leu Leu Ile Val Gln Ala Leu
        660                 665                 670

Arg Asp Asn Leu Glu Pro Gly Thr Phe Asp Ile Gly Gly Leu Tyr Glu
        675                 680                 685

Ser Ile Glu Glu Cys Leu Ile Asn Asp Pro Trp Val Leu Leu Asn Ala
        690                 695                 700

Ser Trp Phe Asn Ser Phe Leu Thr His Ala Leu Lys
705                 710                 715

<210> SEQ ID NO 6
<211> LENGTH: 498
<212> TYPE: PRT
<213> ORGANISM: Influenza A Virus

<400> SEQUENCE: 6

Met Ala Ser Gln Gly Thr Lys Arg Ser Tyr Glu Gln Met Glu Thr Asp
 1               5                  10                  15

Gly Glu Arg Gln Asn Ala Thr Glu Ile Arg Ala Ser Val Gly Arg Met

```
            20                  25                  30
Val Gly Gly Ile Gly Arg Phe Tyr Val Gln Met Cys Thr Glu Leu Lys
        35                  40                  45

Leu Asn Asp His Glu Gly Arg Leu Ile Gln Asn Ser Ile Thr Ile Glu
50                  55                  60

Arg Met Val Leu Ser Ala Phe Asp Glu Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Lys Asp Gly Lys Trp Met Arg Glu Leu Ile Leu His Asp
                100                 105                 110

Lys Glu Glu Ile Met Arg Ile Trp Arg Gln Ala Asn Asn Gly Glu Asp
                115                 120                 125

Ala Thr Ala Gly Leu Thr His Met Met Ile Trp His Ser Asn Leu Asn
                130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
                180                 185                 190

Leu Ile Arg Met Ile Lys Arg Gly Ile Asn Asp Arg Asn Phe Trp Arg
                195                 200                 205

Gly Glu Asn Gly Arg Arg Thr Arg Ile Ala Tyr Glu Arg Met Cys Asn
                210                 215                 220

Ile Leu Lys Gly Lys Phe Gln Thr Ala Ala Gln Arg Ala Met Met Asp
225                 230                 235                 240

Gln Val Arg Glu Gly Arg Asn Pro Gly Asn Ala Glu Ile Glu Asp Leu
                245                 250                 255

Ile Phe Leu Ala Arg Ser Ala Leu Ile Leu Arg Gly Ser Val Ala His
                260                 265                 270

Lys Ser Cys Leu Pro Ala Cys Val Tyr Gly Leu Ala Val Thr Ser Gly
                275                 280                 285

Tyr Asp Phe Glu Lys Glu Gly Tyr Ser Leu Val Gly Ile Asp Pro Phe
                290                 295                 300

Lys Leu Leu Gln Asn Ser Gln Ile Phe Ser Leu Ile Arg Pro Lys Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Asn Phe Ile Arg Gly Thr Lys Val
                340                 345                 350

Ile Pro Arg Gly Gln Leu Thr Thr Arg Gly Val Gln Ile Ala Ser Asn
                355                 360                 365

Glu Asn Met Glu Thr Ile Asp Ser Ser Thr Leu Glu Leu Arg Ser Lys
                370                 375                 380

Tyr Trp Ala Ile Arg Thr Arg Ser Gly Gly Asn Thr Ser Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
                420                 425                 430

Thr Glu Gly Arg Thr Ser Asp Met Arg Thr Glu Ile Ile Arg Met Met
                435                 440                 445
```

```
Glu Asn Ala Lys Ser Glu Asp Val Ser Phe Gln Gly Arg Gly Val Phe
            450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Phe
                485                 490                 495

Asp Ser

<210> SEQ ID NO 7
<211> LENGTH: 252
<212> TYPE: PRT
<213> ORGANISM: Influenza A Virus

<400> SEQUENCE: 7

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
50                  55                  60

Thr Leu Thr Val Pro Ser Glu Arg Gly Leu Gln Arg Arg Arg Phe Val
65                  70                  75                  80

Gln Asn Ala Leu Ser Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Arg
        195                 200                 205

Ala Arg Gln Met Val Gln Ala Met Arg Thr Ile Gly Thr His Pro Ser
210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 8
<211> LENGTH: 230
<212> TYPE: PRT
<213> ORGANISM: Influenza A Virus

<400> SEQUENCE: 8

Met Asp Ser Asn Thr Val Ser Ser Phe Gln Val Asp Cys Phe Leu Trp
1               5                   10                  15
```

His Val Arg Lys Arg Phe Ala Asp Gln Glu Leu Gly Asp Ala Pro Phe
            20                  25                  30
Leu Asp Arg Leu Arg Arg Asp Gln Lys Ser Leu Arg Gly Arg Gly Ser
        35                  40                  45
Thr Leu Gly Leu Asp Ile Glu Thr Ala Thr His Ala Gly Lys Gln Ile
    50                  55                  60
Val Glu Gln Ile Leu Glu Lys Glu Ser Asp Glu Ala Leu Lys Met Thr
65                  70                  75                  80
Ile Ala Ser Val Pro Thr Ser Arg Tyr Leu Thr Asp Met Thr Leu Asp
                85                  90                  95
Glu Met Ser Arg Asp Trp Phe Met Leu Met Pro Lys Gln Lys Val Thr
            100                 105                 110
Gly Ser Leu Cys Ile Arg Met Asp Gln Ala Ile Met Asp Lys Asn Ile
        115                 120                 125
Ile Leu Lys Ala Asn Phe Ser Val Ile Phe Glu Arg Leu Glu Thr Leu
    130                 135                 140
Ile Leu Leu Arg Ala Phe Thr Glu Glu Gly Ala Val Val Gly Glu Ile
145                 150                 155                 160
Ser Pro Leu Pro Ser Leu Pro Gly His Thr Asn Glu Asp Val Lys Asn
                165                 170                 175
Ala Ile Gly Val Leu Ile Gly Gly Leu Lys Trp Asn Asp Asn Thr Val
            180                 185                 190
Arg Ile Ser Glu Thr Leu Gln Arg Phe Ala Trp Arg Ser Ser His Glu
        195                 200                 205
Asn Gly Arg Pro Ser Phe Pro Ser Lys Gln Lys Arg Lys Met Glu Arg
    210                 215                 220
Thr Ile Lys Pro Lys Ile
225                 230

<210> SEQ ID NO 9
<211> LENGTH: 1701
<212> TYPE: DNA
<213> ORGANISM: Influenza A Virus

<400> SEQUENCE: 9
tcatgaagac aaccattatt ttgatactac tgacccattg ggcttacagt caaaacccaa      60
tcagtggcaa caacacagcc acattgtgtc tgggacacca tgcagtagca atgaaacat     120
tggtaaaaac aataagtgat gatcaaattg aggtgacaaa tgctacagaa ttagttcaaa     180
gcatttcaat ggggaaaata tgcaacaact catatagaat tctagatgga agaaattgca     240
cattaataga tgcaatgcta ggagaccccc actgtgacgc ctttcagtat gagaattggg     300
acctctttat agaagaagc agcgctttca gcaattgcta cccatatgac atccctgact     360
atgcatcgct ccgatccatt gtagcatcct caggaacatt ggaattcaca gcagagggat     420
tcacatggac aggtgtcact caaaacggaa gaagtggagc ctgcaaaagg ggatcagccg     480
atagtttctt tagccgactg aattggctaa caaaatctgg aagctcttac ccacattga     540
atgtgacaat gcctaacaat aaaaatttcg acaagctata catctggggg attcatcacc     600
cgagctcaaa tcaagagcag acaaaattgt acatccaaga tcaggacga gtaacagtct     660
caacaaaaag aagtcaacaa acaataatcc ctaacatcgg atctagaccg tgggtcagag     720
gtcaatcagg taggataagc atatactgga ccattgtaaa acctggagat atcctaatga     780
taaacagtaa tggcaactta gttgcaccgc ggggatattt taaattgaaa acagggaaaa     840
gctctgtaat gagatcagat gtacccatag acatttgtgt gtctgaatgt attacaccaa     900

```
atggaagcat ctccaacgac aagccattcc aaaatgtgaa caaagttaca tatggaaaat      960
gccccaagta tatcaggcaa acactttaa agctggccac tgggatgagg aatgtaccag     1020
aaaagcaaat cagaggaatc tttggagcaa tagcgggatt catcgaaaac ggctgggaag    1080
gaatggttga tgggtggtat gggttccgat atcaaaactc tgaaggaaca gggcaagctg    1140
cagatctaaa gagcactcaa gcagccatcg accagattaa tggaaagtta aacagagtga    1200
ttgaaagaac caatgagaaa ttccatcaaa tagagaagga attctcagaa gtagaaagaa    1260
gaattcagga cttggagaaa tatgtagaag acaccaaaat agacctatgg tcctacaatg    1320
cagaattgct ggtggctcta gaaaatcaac atacaattga cttaacagat gcagaaatga    1380
ataaattatt tgagaagact agacgccagt taagagaaaa cgcagaagac atgggaggtg    1440
gatgtttcaa gatttaccac aaatgtgata atgcatgcat tggatcaata gaaatggga    1500 catatgacca ttacatatac agagatgaag cattaaacaa ccgatttcag atcaaaggtg    1560
tagagttgaa atcaggctac aaagattgga ctactgtgga ttcattcgcc atatcatgct    1620
tcttaatttg cgttgttcta ttgggtttca ttatgtgggc ttgccaaaaa ggcaacatca    1680
gatgcaacat ttgcatttga g                                              1701

<210> SEQ ID NO 10
<211> LENGTH: 1413
<212> TYPE: DNA
<213> ORGANISM: Influenza A Virus

<400> SEQUENCE: 10
atgaatccaa atcaaaagat aatagcaatt ggatttgcat cattggggat attaatcatt      60
aatgtcattc tccatgtagt cagcattata gtaacagtac tggtcctcaa taacaataga    120
acagatctga actgcaaagg gacgatcata agagagtaca atgaaacagt aagagtagaa    180
aaaattactc aatggtataa taccagtaca attaagtaca tagagagacc ttcaaatgaa    240
tactacatga caacactga accactttgt gaggcccaag ctttgcacc attttccaaa    300 gataatggaa tacgaattgg gtcgagaggc catgttttg tgataagaga accttttgta    360
tcatgttcgc cctcagaatg tagaacctt tcctcacac agggctcatt actcaatgac    420
aaacattcta acggcacagt aaaggaccga agtccgtata ggactttgat gagtgtcaaa    480
atagggcaat cacctaatgt atatcaagct aggtttgaat cggtggcatg gtcagcaaca    540
gcatgccatg atggaaaaaa atggatgaca gttggagtca cagggcccga caatcaagca    600
attgcagtag tgaactatgg aggtgttccg gttgatatta ttaattcatg gcagggggat    660
attttaagaa cccaagaatc atcatgcacc tgcattaaag gagactgtta ttgggtaatg    720
actgatggac cggcaaatag caagctaaa tataggatat caaagcaaa gatggaaga    780 gtaattggac agactgatat aagtttcaat ggggacaca tagaggagtg ttcttgttac    840
cccaatgaag ggaaggtgga atgcatatgc agggacaatt ggactggaac aaatagacca    900
attctggtaa tatcttctga tctatcgtac acagttggat atttgtgtgc tggcattccc    960
actgacactc taggggaga ggatagtcaa ttcacaggct catgtacaag tccttttggga  1020 aataaaggat acgtgtaaa aggtttcggg tttcgacaag gaactgacgt atgggccgga    1080
aggacaatta gtaggacttc aagatcagga ttcgaaataa taaaaatcag gaatggttgg    1140
acacagaaca gtaaagacca aatcaggagg caagtgatta tcgatgaccc aaattggtca    1200
ggatatagcg gttctttcac attgccggtt gaactaacaa aaaggggatg tttggtcccc    1260
```

-continued

| | |
|---|---|
| tgtttctggg ttgaaatgat tagaggtaaa cctgaagaaa caacaatatg gacctctagc | 1320 |
| agctccattg tgatgtgtgg agtagatcat aaaattgcca gttggtcatg gcacgatgga | 1380 |
| gctattcttc cctttgacat cgataagatg taa | 1413 |

<210> SEQ ID NO 11
<211> LENGTH: 2277
<212> TYPE: DNA
<213> ORGANISM: Influenza A Virus

<400> SEQUENCE: 11

| | |
|---|---|
| atggatgtca atccgactct acttttctta aaggtgccag cgcaaaatgc tataagcaca | 60 |
| acatttcctt atactggaga tcctccctac agtcatggaa cagggacagg atacaccatg | 120 |
| gatactgtca acagaacaca ccaatattca gaaaaaggga atggacaac aaacactgag | 180 |
| attggagcac acaacttaa tccaatcgat ggaccacttc ctgaagacaa tgaaccaagt | 240 |
| gggtacgccc aaacagattg tgtattgaa gcaatggctt ccttgaaga atcccatccc | 300 |
| ggaatctttg aaaattcgtg tcttgaaacg atggaggtga ttcagcagac aagagtggac | 360 |
| aaactaacac aaggccgaca aacttatgat tggaccttga ataggaatca acctgccgca | 420 |
| acagcacttg ctaatacgat tgaagtattc agatcaaatg gtctgacttc caatgaatcg | 480 |
| gggagattga tggacttcct caaagatgtc atggagtcca tgaacaagga agaaatggaa | 540 |
| ataacaacac acttccaacg aagagaaga gtaagagaca catgacaaa gagaatggta | 600 |
| acacagagaa ccatagggaa gaaaaacaa cgattaaaca gaaagagcta tctaatcaga | 660 |
| acattaaccc taaacacaat gaccaaggac gctgagagag ggaaattgaa cgacgagca | 720 |
| atcgctaccc cagggatgca gataagaggg tttgtatatt ttgttgaaac actagcccga | 780 |
| agaatatgtg aaaagcttga acaatcagga ttgccagttg gcggtaatga aaaaaggcc | 840 |
| aaactggcta atgtcgtcag aaaatgatg actaattccc aagacactga actctccttc | 900 |
| accatcactg gggacaatac caatggaat gaaaatcaga acccacgcat attcctggca | 960 |
| atgatcacat acataactag aaaccagcca gaatggttca gaaatgttct aagcattgca | 1020 |
| ccgattatgt tctcaaataa aatggcaaga ctggggaaag gatatatgtt tgaaagcaaa | 1080 |
| agtatgaaat tgagaactca ataccagca ggaatgcttg caagcattga cctgaaatat | 1140 |
| ttcaatgatc aacaaaaaaa gaaaattgaa aagatacgac cacttctggt tgacgggact | 1200 |
| gcttcactga gtcctggcat gatgatggga atgttcaaca tgttgagcac tgtgctaggt | 1260 |
| gtatccatat aaacctgggg ccagaggaaa tacacaaaga ccacatactg gtgggatggt | 1320 |
| ctgcaatcat ccgatgactt tgctttgata gtgaatgcgc taatcatga aggaatacaa | 1380 |
| gctggagtag acagattcta taggacttgc aaactggtcg ggatcaacat gagcaaaaag | 1440 |
| aagtcctaca taaatagaac tggaacattc gaattcacaa gctttttcta ccggtatggt | 1500 |
| tttgtagcca atttcagcat ggaactaccc agttttgggg tttccggaat aaatgaatct | 1560 |
| gcagacatga gcattggagt gacagtcatc aaaaacaaca tgataaataa tgatctcggt | 1620 |
| cctgccacgg cacaaatggc actccaactc ttcattaagg attatcggta cacataccgg | 1680 |
| tgccatagag gtgataccca gatacaaacc agaagatctt tgagttgaa gaaactgtgg | 1740 |
| gaacagactc gatcaaagac tggtctactg gtatcagatg ggggtccaaa cctatataac | 1800 |
| atcagaaacc tacacatccc ggaagtctgt ttaaaatggg agctaatgga tgaagattat | 1860 |
| aaggggaggc tatgcaatcc attgaatcct ttcgttagtc acaaagaaat tgaatcagtc | 1920 |
| aacagtgcag tagtaatgcc tgcgcatggc cctgccaaaa gcatggagta tgatgctgtt | 1980 |

| | |
|---|---|
| gcaacaacac attcttggat ccccaagagg aaccggtcca tattgaacac aagccaaagg | 2040 |
| ggaatactcg aagatgagca gatgtatcag aaatgctgca acctgtttga aaaattcttc | 2100 |
| cccagcagct catacagaag accagtcggg atttctagta tggttgaggc catggtgtcc | 2160 |
| agggcccgca ttgatgcacg aattgacttc gaatctggac ggataaagaa ggatgagttc | 2220 |
| gctgagatca tgaagatctg ttccaccatt gaagagctca gacggcaaaa atagtga | 2277 |

<210> SEQ ID NO 12
<211> LENGTH: 2281
<212> TYPE: DNA
<213> ORGANISM: Influenza A Virus

<400> SEQUENCE: 12

| | |
|---|---|
| atggagagaa taaaagaact gagagatctg atgttacaat cccgcacccg cgagatacta | 60 |
| acaaaaacta ctgtggacca catggccata atcaagaaat acacatcagg aagacaagag | 120 |
| aagaaccctg cacttaggat gaatggatg atggcaatga aatacccaat tacagcagat | 180 |
| aagaggataa tggagatgat tcctgagaga aatgaacagg acaaaccct tggagcaaaa | 240 |
| acgaacgatg ctggctcaga ccgcgtaatg gtatcacctc tggcagtgac atggtggaat | 300 |
| aggaatggac aacaacaag cacaattcat tatccaaaag tctacaaaac ttattttgaa | 360 |
| aaggttgaaa gattgaaaca cggaaccttt ggccccgttc attttaggaa tcaagtcaag | 420 |
| ataagacgaa gagttgatgt aaaccctggt cacgcggacc tcagtgccaa agaagcacaa | 480 |
| gatgtgatca tggaagttgt tttcccaaat gaagtgggag ccagaattct aacatcggaa | 540 |
| tcacaactaa caataaccaa agagaaaaag gaagaacttc aggactgcaa aattgctccc | 600 |
| ttgatggtag catacatgct agaaagagag ttggtccgaa aaacaaggtt cctcccagta | 660 |
| gcaggcggaa caagcagtgt atacattgaa gtgttgcatc tgactcaggg aacatgctgg | 720 |
| gagcaaatgt acaccccagg aggagaagtt agaaacgatg atattgatca agtttaatt | 780 |
| attgcagccc ggaacatagt gagaagagca acagtatcag cagatccact agcatcccta | 840 |
| ctggaaatgt gccacagtac acagattggt ggaataagga tggtagacat ccttaagcag | 900 |
| aatccaacag aggaacaagc tgtggatata tgcaaagcag caatgggatt gagaattagc | 960 |
| tcatcattca gctttggtgg attcaccttc aagagaacaa gtggatcatc agtcaagaga | 1020 |
| gaagaagaaa tgcttacggg caaccttcaa acattgaaaa taagagtgca tgagggctat | 1080 |
| gaagaattca atggtcgg aagaagagca acagccattc tcagaaaggc aaccagaaga | 1140 |
| ttgattcaat tgatagtaag tgggagagat gaacagtcaa ttgctgaagc aataattgta | 1200 |
| gccatggtgt tttcgcaaga agattgcatg ataaaagcag ttcgaggcga tttgaacttt | 1260 |
| gttaatagag caaatcagcg cttgaacccc atgcatcaac tcttgaggca tttccaaaag | 1320 |
| gatgcaaaag tgcttttcca aaattggggg attgaaccca tcgacaatgt aatgggaatg | 1380 |
| attggaatat gcctgacat gacccccaagc accgagatgt cattgagagg agtgagagtc | 1440 |
| agcaaaatgg gagtggatga gtactccagc actgagagag tggtggtgag cattgaccgt | 1500 |
| tttttaagag ttcgggatca aaggggaaac atactactgt cccctgaaga agtcagtgaa | 1560 |
| acacaaggaa cggaaaagct gacaataatt tattcgtcat caatgatgtg ggagattaat | 1620 |
| ggtcccgaat cagtgttggt caatacttat caatggatca tcaggaactg ggaaattgta | 1680 |
| aaaattcagt ggtcacagga ccccacaatg ttatacaata agatagaatt tgagccattc | 1740 |
| caatccctgg tccctagggc taccagaagc caatacagcg gtttcgtaag aaccctgttt | 1800 |

| | |
|---|---|
| cagcaaatgc gagatgtact tggaacattt gatactgctc aaataataaa actcctccct | 1860 |
| tttgccgctg ctcctccgga acagagtagg atgcagttct cttctttgac tgttaatgta | 1920 |
| agaggttcgg gaatgaggat acttgtaaga ggcaattccc cagtgttcaa ctacaataaa | 1980 |
| gccactaaaa ggctcacagt cctcggaaag gatgcaggtg cgcttactga ggacccagat | 2040 |
| gaaggtacgg ctggagtaga atctgctgtt ctaagagggt ttctcatttt aggtaaagaa | 2100 |
| aataagagat atggcccagc actaagcatc aatgaactaa gcaaacttgc aaaaggggag | 2160 |
| aaagccaatg tactaattgg gcaaggggac gtagtgttgg taatgaaacg gaaacgtgac | 2220 |
| tctagcatac ttactgacag ccagacagcg accaaaagga ttcggatggc catcaattag | 2280 |
| t | 2281 |

<210> SEQ ID NO 13
<211> LENGTH: 2209
<212> TYPE: DNA
<213> ORGANISM: Influenza A Virus

<400> SEQUENCE: 13

| | |
|---|---|
| atggaagact tgtgcgacaa atgcttcaat ccaatgatcg tcgagcttgc ggaaaaggca | 60 |
| atgaaagaat atggagagga cccgaaaatc gaaacaaaca atttgcagc aatatgcact | 120 |
| cacttggaag tctgcttcat gtactcggat ttccacttta ttaatgaact gagtgagtca | 180 |
| gtggtcatag agtctggtga cccaaatgct cttttgaaac acagatttga atcattgag | 240 |
| gggagagatc gaacaatggc atggacagta gtaaacagca tctgcaacac cacaagagct | 300 |
| gaaaaaccta aatttcttcc agatttatac gactataagg agaacagatt tgttgaaatt | 360 |
| ggtgtgacaa ggagagaagt tcacatatac tacctggaga aggccaacaa aataaagtct | 420 |
| gagaaaacac atatccacat tttctcattt acaggagagg aaatggctac aaaagcggac | 480 |
| tatactcttg atgaagagag tagagccagg atcaagacca gactattcac tataagacaa | 540 |
| gaaatggcca gtagaggcct ctgggattcc tttgtcagt ccgagagagg cgaagagaca | 600 |
| attgaagaaa gatttgaaat cacagggacg atgcgcaagc ttgccaatta cagtctccca | 660 |
| ccgaacttct ccagccttga aaattttaga gtctatgtgg atggattcga accgaacggc | 720 |
| tgcattgaga gtaagctttc tcaaatgtcc aaagaagtaa atgccagaat cgaaccattt | 780 |
| tcaaagacaa caccccgacc actcaaaatg ccaggtggtc caccctgcca tcagcgatct | 840 |
| aaattcctgc taatggatgc tctgaaactg agcattgagg acccaagtca cgagggagag | 900 |
| ggaataccac tatatgatgc catcaaatgc atgaaaactt tctttggatg aaagagccc | 960 |
| agtattgtta accacatga aagggtata acccgaact atctccaaac ttggaagcaa | 1020 |
| gtattagcag aattacaaga ccttgagaac gaagaaaagg accccaagac caagaatatg | 1080 |
| aaaaaaacaa gccaattgaa atgggcactt agtgaaaata tggcaccaga aaagtggat | 1140 |
| tttgaggatt gtaaagacat cagtgattta aaacagtatg acagtgatga gccagaaaca | 1200 |
| aggtctcttg caagttggat tcaaagtgag ttcaacaaag cttgtgaact gacagattca | 1260 |
| agctggatag agctcgatga aattggggag atgttgccc aatagaata cattgcgagc | 1320 |
| atgaggagaa attatttac tgctgaggtt tcccattgta agcaacaga atatataatg | 1380 |
| aagggagtgt acatcaacac tgctctactc aatgcatcct gtgctgcgat ggatgaattc | 1440 |
| caattaattc cgatgataag taaatgcagg accaaagaag ggagaaggaa gacaaattta | 1500 |
| tatgattca tagtaaaggg aaggtcccat ttaagaaatg atactgacgt ggtgaactt | 1560 |
| gtaagtatgg aattttctct cactgatcca agatttgagc cacacaaatg ggaaaatac | 1620 |

| | |
|---|---|
| tgcgttctag aaattggaga catgcttcta agaactgctg taggtcaagt gtcaagaccc | 1680 |
| atgttttgt atgtaaggac aaatggaacc tctaaaatta aaatgaaatg gggaatggaa | 1740 |
| atgaggcgct gcctccttca gtctctgcaa cagattgaaa gcatgatcga agctgagtcc | 1800 |
| tcagtcaaag aaaaggacat gaccaaagaa ttttttgaga caaatcaga gacatggcct | 1860 |
| ataggagagt cccccaaagg agtggaagag ggctcaatcg ggaaggtttg caggaccta | 1920 |
| ttagcaaaat ctgtgtttaa cagtttgtat gcatctccac aactggaagg ttttcagct | 1980 |
| gaatctagga aattacttct cattgttcag gctcttaggg ataacctgga acctggaacc | 2040 |
| tttgatattg gggggttata tgaatcaatt gaggagtgcc tgattaatga tccctgggtt | 2100 |
| ttgcttaatg catcttggtt caactccttc cttacacatg cactgaagta gttgtggcaa | 2160 |
| tgctactatt tgctatccat actgtccaaa aaagtaccttt gtttctact | 2209 |

<210> SEQ ID NO 14
<211> LENGTH: 1498
<212> TYPE: DNA
<213> ORGANISM: Influenza A Virus

<400> SEQUENCE: 14

| | |
|---|---|
| atggcgtctc aaggcaccaa acgatcctat gaacagatgg aaactgatgg ggaacgccag | 60 |
| aatgcaactg aaatcagagc atctgtcgga aggatggtgg aggaatcgg ccggttttat | 120 |
| gttcagatgt gtactgagct aaactaaac gaccatgaag ggcggctgat tcagaacagc | 180 |
| ataacaatag aaaggatggt actttcggca ttcgacgaaa aagagaaacaa gtatctcgag | 240 |
| gagcatccca gtgctgggaa agaccctaag aaaacaggag gcccgatata cagaaggaaa | 300 |
| gatgggaaat ggatgaggga actcatcctc catgataaag aagaaatcat gagaatctgg | 360 |
| cgtcaggcca acaatggtga agacgctact gctggtctta ctcatatgat gatctggcac | 420 |
| tccaatctca atgacaccac ataccaaaga acaagggctc ttgttcggac tgggatggat | 480 |
| cccagaatgt gctctctgat gcaaggctca accctcccac ggagatctgg agccgctggt | 540 |
| gctgcagtaa aggtgttgg aacaatggta atggaactca tcagaatgat caaacgcgga | 600 |
| ataaatgatc ggaattctg agagggtgaa atggtcgaa gaaccagaat tgcttatgaa | 660 |
| agaatgtgca atatcctcaa agggaaattt cagacagcag cacaacgggc tatgatggac | 720 |
| caggtgaggg aaggccgcaa tcctggaaac gctgagattg aggatctcat tttcttggca | 780 |
| cgatcagcac ttatttgag aggatcagta gcccataaat catgcctacc tgcctgtgtt | 840 |
| tatgccttg cagtaaccag tgggtatgac tttgagaagg aaggatactc tctggttgga | 900 |
| attgatcctt tcaaactact ccagaacagt caattttca gtctaatcag accaaaagaa | 960 |
| aacccagcac acaagagcca gttggtgtgg atggcatgcc attctgcagc atttgaggac | 1020 |
| ctgagagttt taaatttcat tagaggaacc aaagtaatcc caagaggaca gttaacaacc | 1080 |
| agaggagttc aaatagcttc aaatgaaaac atggagacaa tagattctag cacacttgaa | 1140 |
| ctgagaagca atatattgggc aataaggacc agaagcggag aaacaccag tcaacagaga | 1200 |
| gcatctgcag acagataag tgtgcaacct actttctcag tacagagaaa tcttcccttt | 1260 |
| gagagagcaa ccattatggc tgcattcact ggtaacactg aagggaggac ttccgacatg | 1320 |
| agaacggaaa tcataaggat gatggaaaat gccaaatcag aagatgtgtc tttccagggg | 1380 |
| cggggagtct tcgagctctc ggacgaaaag gcaacgaacc cgatcgtgcc ttcctttgac | 1440 |
| atgagcaatg aagggtctta tttcttcgga gacaatgctg aggagtttga cagttaaa | 1498 |

<210> SEQ ID NO 15
<211> LENGTH: 982
<212> TYPE: DNA
<213> ORGANISM: Influenza A Virus

<400> SEQUENCE: 15

| | | | | | |
|---|---|---|---|---|---|
| atgagtcttc | taaccgaggt | cgaaacgtac | gttctctcta | tcgtaccatc | aggccccctc | 60 |
| aaagccgaga | tcgcgcagag | acttgaagat | gtctttgcag | ggaagaacac | cgatcttgag | 120 |
| gcactcatgg | aatggctaaa | gacaagacca | atcctgtcac | ctctgactaa | agggatttta | 180 |
| ggatttgtat | tcacgctcac | cgtgcccagt | gagcgaggac | tgcagcgtag | acgctttgtc | 240 |
| caaaatgccc | ttagtggaaa | cggagatcca | aacaacatgg | acagagcagt | aaaactgtac | 300 |
| aggaagctta | aaagagaaat | aacattccat | ggggcaaaag | aggtggcact | cagctattcc | 360 |
| actggtgcac | tagccagctg | catgggactc | atatacaaca | gaatgggaac | tgttacaacc | 420 |
| gaagtggcat | ttggcctggt | atgcgccaca | tgtgaacaga | ttgctgattc | ccagcatcgg | 480 |
| tctcacaggc | agatggtgac | aacaaccaac | ccattaatca | gacatgaaaa | cagaatggta | 540 |
| ttagccagta | ccacggctaa | agccatggaa | cagatggcag | gatcgagtga | gcaggcagca | 600 |
| gaggccatgg | aggttgctag | tagggctagg | cagatggtac | aggcaatgag | aaccattggg | 660 |
| acccacccta | gctccagtgc | cggtttgaaa | gatgatctcc | ttgaaaattt | acaggcctac | 720 |
| cagaaacgga | tgggagtgca | aatgcagcga | ttcaagtgat | cctctcgtta | ttgcagcaag | 780 |
| tatcattggg | atcttgcact | tgatattgtg | gattcttgat | cgtctttcct | tcaaattcat | 840 |
| ttatcgtcgc | cttaaatacg | ggttgaaaag | agggccttct | acggaaggag | tacctgagtc | 900 |
| tatgagggaa | gaatatcggc | aggaacagca | gaatgctgtg | gatgttgacg | atggtcattt | 960 |
| tgtcaacata | gagctggagt | aa | | | | 982 |

<210> SEQ ID NO 16
<211> LENGTH: 838
<212> TYPE: DNA
<213> ORGANISM: Influenza A Virus

<400> SEQUENCE: 16

| | | | | | |
|---|---|---|---|---|---|
| atggattcca | acactgtgtc | aagctttcag | gtagactgtt | ttctttggca | tgtccgcaaa | 60 |
| cgattcgcag | accaagaact | gggtgatgcc | ccattccttg | accggcttcg | ccgagaccag | 120 |
| aagtccctaa | ggggaagagg | tagcactctt | ggtctggaca | tcgaaacagc | cactcatgca | 180 |
| ggaaagcaga | tagtggagca | gattctggaa | aaggaatcag | atgaggcact | aaaaatgacc | 240 |
| attgcctctg | ttcctacttc | acgctactta | actgacatga | ctcttgatga | gatgtcaaga | 300 |
| gactggttca | tgctcatgcc | caagcaaaaa | gtaacaggct | ccctatgtat | aagaatggac | 360 |
| caggcaatca | tggataagaa | catcatactt | aaagcaaact | ttagtgtgat | ttttgaaagg | 420 |
| ctggaaacac | taatactact | tagagccttc | accgaagaag | gagcagtcgt | tggcgaaatt | 480 |
| tcaccattac | cttctcttcc | aggacatact | aatgaggatg | tcaaaaatgc | aattgggatc | 540 |
| ctcatcggag | gacttaaatg | gaatgataat | acggttagaa | tctctgaaac | tctacagaga | 600 |
| ttcgcttgga | gaagcagtca | tgagaatggg | agaccttcat | tcccttcaaa | gcagaaacga | 660 |
| aaaatggaga | gaacaattaa | gccaaaaatt | tgaagaaata | agatggttga | ttgaagaagt | 720 |
| gcgacataga | ttgaaaaata | cagaaaatag | ttttgaacaa | ataacattta | tgcaagcctt | 780 |
| acaactattg | cttgaagtag | aacaagagat | aagaactttc | tcgtttcagc | ttatttaa | 838 |

```
<210> SEQ ID NO 17
<211> LENGTH: 97
<212> TYPE: PRT
<213> ORGANISM: Influenza A Virus

<400> SEQUENCE: 17

Met Ser Leu Leu Thr Glu Val Glu Thr Pro Thr Arg Asn Gly Trp Glu
1               5                   10                  15

Cys Lys Cys Ser Asp Ser Ser Asp Pro Leu Val Ile Ala Ala Ser Ile
            20                  25                  30

Ile Gly Ile Leu His Leu Ile Leu Trp Ile Leu Asp Arg Leu Phe Phe
        35                  40                  45

Lys Phe Ile Tyr Arg Arg Leu Lys Tyr Gly Leu Lys Arg Gly Pro Ser
50                  55                  60

Thr Glu Gly Val Pro Glu Ser Met Arg Glu Glu Tyr Arg Gln Glu Gln
65                  70                  75                  80

Gln Asn Ala Val Asp Val Asp Asp Gly His Phe Val Asn Ile Glu Leu
                85                  90                  95

Glu

<210> SEQ ID NO 18
<211> LENGTH: 119
<212> TYPE: PRT
<213> ORGANISM: Influenza A Virus

<400> SEQUENCE: 18

Met Asp Ser Asn Thr Val Ser Ser Phe Gln Leu Met Arg Met Ser L

```
Lys Ile Cys Asn Asn Ser Tyr Arg Ile Leu Asp Gly Arg Asn Cys Thr
 65                  70                  75                  80

Leu Ile Asp Ala Met Leu Gly Asp Pro His Cys Asp Ala Phe Gln Tyr
                 85                  90                  95

Glu Asn Trp Asp Leu Phe Ile Glu Arg Ser Ser Ala Phe Ser Asn Cys
            100                 105                 110

Tyr Pro Tyr Asp Ile Pro Asp Tyr Ala Ser Leu Arg Ser Ile Val Ala
        115                 120                 125

Ser Ser Gly Thr Leu Glu Phe Thr Ala Glu Gly Phe Thr Trp Thr Gly
130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Gln Glu Gln Thr Lys
        195                 200                 205

Leu Tyr Ile Gln Glu Ser Gly Arg Val Thr Val Ser Thr Lys Arg Ser
210                 215                 220

Gln Gln Thr Ile Ile Pro Asn Ile Gly Ser Arg Pro Trp Val Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
            260                 265                 270

Phe Lys Leu Lys Thr Gly Lys Ser Ser Val Met Arg Ser Asp Val Pro
        275                 280                 285

Ile Asp Ile Cys Val Ser Glu Cys Ile Thr Pro Asn Gly Ser Ile Ser
290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Ile Arg
            340

<210> SEQ ID NO 20
<211> LENGTH: 344
<212> TYPE: PRT
<213> ORGANISM: Influenza A Virus

<400> SEQUENCE: 20

Met Lys Thr Thr Ile Ile Leu Ile Leu Leu Thr His Trp Ala Tyr Ser
 1               5                  10                  15

Gln Asn Pro Ile Ser Gly Asn Asn Thr Ala Thr Leu Cys Leu Gly His
             20                  25                  30

His Ala Val Ala Asn Gly Thr Leu Val Lys Thr Ile Ser Asp Asp Gln
         35                  40                  45

Ile Glu Val Thr Asn Ala Thr Glu Leu Val Gln Ser Ile Ser Met Gly
     50                  55                  60

Lys Ile Cys Asn Asn Ser Tyr Arg Ile Leu Asp Gly Arg Asn Cys Thr
 65                  70                  75                  80

Leu Ile Asp Ala Met Leu Gly Asp Pro His Cys Asp Val Phe Gln Tyr
                 85                  90                  95
```

-continued

```
Glu Asn Trp Asp Leu Phe Ile Glu Arg Ser Ser Ala Phe Ser Asn Cys
            100                 105                 110
Tyr Pro Tyr Asp Ile Pro Asp Tyr Ala Ser Leu Arg Ser Ile Val Ala
            115                 120                 125
Ser Ser Gly Thr Leu Glu Phe Thr Ala Glu Gly Phe Thr Trp Thr Gly
130                 135                 140
Val Thr Gln Asn Gly Arg Ser Gly Ala Cys Lys Arg Gly Ser Ala Asp
145                 150                 155                 160
Ser Phe Phe Ser Arg Leu Asn Trp Leu Thr Lys Ser Gly Asn Ser Tyr
                165                 170                 175
Pro Thr Leu Asn Val Thr Met Pro Asn Asn Lys Asn Phe Asp Lys Leu
            180                 185                 190
Tyr Ile Trp Gly Ile His His Pro Ser Ser Asn Gln Glu Gln Thr Lys
            195                 200                 205
Leu Tyr Ile Gln Glu Ser Gly Arg Val Thr Val Ser Thr Lys Arg Ser
        210                 215                 220
Gln Gln Thr Ile Ile Pro Asn Ile Gly Ser Arg Pro Trp Val Arg Gly
225                 230                 235                 240
Gln Ser Gly Arg Ile Ser Ile Tyr Trp Thr Ile Val Lys Pro Gly Asp
                245                 250                 255
Ile Leu Met Ile Asn Ser Asn Gly Asn Leu Val Ala Pro Arg Gly Tyr
            260                 265                 270
Phe Lys Leu Lys Thr Gly Lys Ser Ser Val Met Arg Ser Asp Ala Pro
            275                 280                 285
Ile Asp Ile Cys Val Ser Glu Cys Ile Thr Pro Asn Gly Ser Ile Ser
            290                 295                 300
Asn Asp Lys Pro Phe Gln Asn Val Asn Lys Val Thr Tyr Gly Lys Cys
305                 310                 315                 320
Pro Lys Tyr Ile Arg Gln Asn Thr Leu Lys Leu Ala Thr Gly Met Arg
                325                 330                 335
Asn Val Pro Glu Lys Gln Ile Arg
            340
```

US 9,180,181 B2

H3 INFLUENZA A VIRUS

CROSS-REFERENCE TO RELATED APPLICATION

This application is a continuation of U.S. patent application Ser. No. 13/839,111, filed Mar. 15, 2013, which is a continuation of U.S. patent application Ser. No. 12/503,712, filed Jul. 15, 2009, which is a divisional of U.S. patent application Ser. No. 11/033,248, filed Jan. 11, 2005, which application is incorporated herein by reference.

STATEMENT OF GOVERNMENT RIGHTS

The invention was made, at least in part, with a grant from the Government of the United States of America (grant 2001-35204-10184 from the United States Department of Agriculture). The Government may have certain rights to the invention.

BACKGROUND

Influenza is a major respiratory disease in some mammals including horses and is responsible for substantial morbidity and economic losses each year. In addition, influenza virus infections can cause severe systemic disease in some avian species, leading to death. The segmented nature of the influenza virus genome allows for reassortment of segments during virus replication in cells infected with two or more influenza viruses. The reassortment of segments, combined with genetic mutation and drift, can give rise to a myriad of divergent strains of influenza virus over time. The new strains exhibit antigenic variation in their hemagglutinin (HA) and/or neuraminidase (NA) proteins, and in particular the gene coding for the HA protein has a high rate of variability. The predominant current practice for the prevention of flu is vaccination. Most commonly, whole virus vaccines are used. As the influenza HA protein is the major target antigen for the protective immune responses of a host to the virus and is highly variable, the isolation of influenza virus and the identification and characterization of the HA antigen in viruses associated with recent outbreaks is important for vaccine production. Based on prevalence and prediction, a vaccine is designed to stimulate a protective immune response against the predominant and expected influenza virus strains (Park et al., 2004).

There are three general types of influenza viruses, Type A, Type B and Type C, which are defined by the absence of serological crossreactivity between their internal proteins. Influenza Type A viruses are further classified into subtypes based on antigenic and genetic differences of their glycoproteins, the HA and NA proteins. All the known HA and NA subtypes (H1 to H15 and N1 to N9) have been isolated from aquatic birds, which are though to act as a natural reservoir for influenza. H7N7 and H3N8 Type A viruses are the most common causes of equine influenza, and those subtypes are generally incorporated into equine influenza vaccines.

Thus, there is a continuing need to isolate new influenza virus isolates, e.g., for vaccine production.

SUMMARY OF THE INVENTION

The invention provides isolated H3 equine derived influenza type A virus that was isolated from a foal that succumbed to a fatal pneumonia, which virus has characteristic substitutions at residues 78 and 159 of HA (numbering of positions is that in the mature protein which lacks a 15 amino acid signal peptide), i.e., the residue at position 78 of HA is not valine and the residue at position 159 is not asparagine. In one embodiment, the isolated H3 influenza A virus of the invention has a conservative substitution at residue 78, e.g., a valine to an alanine substitution, and a nonconservative substitution at residue 159, e.g., an asparagine to a serine substitution. In one embodiment, the isolated H3 influenza A virus of the invention has a residue other than methionine at position 29, e.g., a nonconservative substitution, a residue other than lysine at position 54, e.g., a nonconservative substitution, a residue other than serine at position 83, e.g., a nonconservative substitution, a residue other than asparagine at position 92, e.g., a nonconservative substitution, a residue other than leucine at position 222, e.g., a nonconservative substitution, a residue other than alanine at position 272, e.g., a conservative substitution, and/or a residue other than threonine at position 328, e.g., a conservative substitution. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: threonine-valine-leucine-isoleucine-alanine; phenylalanine-tyrosine; lysine-arginine; alanine-valine; glutamic-aspartic; and asparagine-glutamine.

In one embodiment, the influenza virus of the invention includes one or more viral proteins (polypeptides) having substantially the same amino acid sequence as one of SEQ ID NOs:1-8, 17 and/or 18, so long as the HA has the characteristic substitutions at residues 78 and 159. An amino acid sequence which is substantially the same as a reference sequence has at least 95%, e.g., 96%, 97%, 98% or 99%, amino acid sequence identity to that reference sequence, and may include sequences with deletions, e.g., those that result in a deleted viral protein having substantially the same activity or capable of being expressed at substantially the same level as the corresponding full-length, mature viral protein, insertions, e.g., those that result in a modified viral protein having substantially the same activity or capable of being expressed at substantially the same level as the corresponding full-length, mature viral protein, and/or substitutions, e.g., those that result in a viral protein having substantially the same activity or capable of being expressed at substantially the same level as the reference protein. In one embodiment, the one or more residues which are not identical to those in the reference sequence may be conservative or nonconservative substitutions which one or more substitutions do not substantially alter the expressed level or activity of the protein with the substitution(s), and/or the level of virus obtained from a cell infected with a virus having that protein. As used herein, "substantially the same expressed level or activity" includes a detectable protein level that is about 80%, 90% or more, the protein level, or a measurable activity that is about 30%, 50%, 90%, e.g., up to 100% or more, the activity, of a full-length mature polypeptide corresponding to one of SEQ ID NOs:1-8, 17 or 18. In one embodiment, the virus comprises a polypeptide with one or more, for instance, 2, 5, 10, 15, 20 or more, amino acid substitutions, e.g., conservative substitutions of up to 5% of the residues of the full-length, mature form of a polypeptide having SEQ ID NOs:1-8, 17 or 18. The isolated virus of the invention may be employed alone or with one or more other virus isolates, e.g., other influenza virus isolates, in a vaccine, to raise virus-specific antisera, in gene therapy, and/or in diagnostics. Accordingly, the invention provides host cells infected with the virus of the invention, and isolated antibody specific for the virus.

The invention also provides an isolated nucleic acid molecule (polynucleotide) comprising a nucleic acid segment corresponding to at least one of the proteins of the virus of the invention, a portion of the nucleic acid segment for a viral protein having substantially the same level or activity as a corresponding polypeptide encoded by one of SEQ ID NOs: 1-8, 17 or 18, or the complement of the nucleic acid molecule. In one embodiment, the isolated nucleic acid molecule encodes a polypeptide which has substantially the same amino acid sequence, e.g., has at least 95%, e.g., 96%, 97%, 98% or 99%, contiguous amino acid sequence identity to a polypeptide having one of SEQ ID NOs:1-8, 17 or 18. In one embodiment, the isolated nucleic acid molecule comprises a nucleotide sequence which is substantially the same as, e.g., has at least 50%, e.g., 60%, 70%, 80% or 90% or more, contiguous nucleic acid sequence identity to, one of SEQ ID NOs:9-16, or the complement thereof, and encodes a polypeptide having at least 95%, e.g., 96%, 97%, 98% or 99%, contiguous amino acid sequence identity to a polypeptide having one of SEQ ID NOs:1-8, 17 or 18.

The isolated nucleic acid molecule of the invention may be employed in a vector to express influenza proteins, e.g., for recombinant protein vaccine production or to raise antisera, as a nucleic acid vaccine, for use in diagnostics or, for vRNA production, to prepare chimeric genes, e.g., with other viral genes including other influenza virus genes, and/or to prepare recombinant virus, e.g., see Neumann et al. (1999) which is incorporated by reference herein. Thus, the invention also provides isolated viral polypeptides, recombinant virus, and host cells contacted with the nucleic acid molecule(s) and/or recombinant virus of the invention, as well as isolated virus-specific antibodies, for instance, obtained from mammals infected with the virus or immunized with an isolated viral polypeptide or polynucleotide encoding one or more viral polypeptides.

The invention further provides at least one of the following isolated vectors, for instance, one or more isolated influenza virus vectors, or a composition comprising the one or more vectors: a vector comprising a promoter operably linked to an influenza virus PA DNA for a PA having substantially the same amino acid sequence as SEQ ID NO:5 linked to a transcription termination sequence, a vector comprising a promoter operably linked to an influenza virus PB1 DNA for a PB1 having substantially the same amino acid sequence as SEQ ID NO:3 linked to a transcription termination sequence, a vector comprising a promoter operably linked to an influenza virus PB2 DNA for a PB2 having substantially the same amino acid sequence as SEQ ID NO:4 linked to a transcription termination sequence, a vector comprising a promoter operably linked to an influenza virus HA DNA for a HA having substantially the same amino acid sequence as SEQ ID NO:1 linked to a transcription termination sequence, a vector comprising a promoter operably linked to an influenza virus NP DNA for a NP having substantially the same amino acid sequence as SEQ ID NO:6 linked to a transcription termination sequence, a vector comprising a promoter operably linked to an influenza virus NA DNA for a NA having substantially the same amino acid sequence as SEQ ID NO:2 linked to a transcription termination sequence, a vector comprising a promoter operably linked to an influenza virus M DNA for a M a having substantially the same amino acid sequence as SEQ ID NO:7 (M1) and/or SEQ ID NO:17 (M2), linked to a transcription termination sequence, and/or a vector comprising a promoter operably linked to an influenza virus NS DNA for a NS having substantially the same amino acid sequence as SEQ ID NO:8 (NS1) and/or SEQ ID NO:18 (NS2), linked to a transcription termination sequence. Optionally, two vectors may be employed in place of the vector comprising a promoter operably linked to an influenza virus M DNA linked to a transcription termination sequence, e.g., a vector comprising a promoter operably linked to an influenza virus M1 DNA linked to a transcription termination sequence and a vector comprising a promoter operably linked to an influenza virus M2 DNA linked to a transcription termination sequence. Optionally, two vectors may be employed in place of the vector comprising a promoter operably linked to an influenza virus NS DNA linked to a transcription termination sequence, e.g., a vector comprising a promoter operably linked to an influenza virus NS1 DNA linked to a transcription termination sequence and a vector comprising a promoter operably linked to an influenza virus NS2 DNA linked to a transcription termination sequence. An influenza virus vector is one which includes at least 5' and 3' noncoding influenza virus sequences.

Hence, the invention provides vectors, e.g., plasmids, which encode influenza virus proteins, and/or encode influenza vRNA, both native and recombinant vRNA. Thus, a vector of the invention may encode an influenza virus protein (sense) or vRNA (antisense). Any suitable promoter or transcription termination sequence may be employed to express a protein or peptide, e.g., a viral protein or peptide, a protein or peptide of a nonviral pathogen, or a therapeutic protein or peptide. In one embodiment, to express vRNA, the promoter is a RNA polymerase I promoter, a RNA polymerase II promoter, a RNA polymerase III promoter, a T3 promoter or a T7 promoter. Optionally the vector comprises a transcription termination sequence such as a RNA polymerase I transcription termination sequence, a RNA polymerase II transcription termination sequence, a RNA polymerase III transcription termination sequence, or a ribozyme.

A composition of the invention may also comprise a gene or open reading frame of interest, e.g., a foreign gene encoding an immunogenic peptide or protein useful as a vaccine. Thus, another embodiment of the invention comprises a composition of the invention as described above in which one of the influenza virus genes in the vectors is replaced with a foreign gene, or the composition further comprises, in addition to all the influenza virus genes, a vector comprising a promoter linked to 5' influenza virus sequences linked to a desired nucleic acid sequence, e.g., a cDNA of interest, linked to 3' influenza virus sequences linked to a transcription termination sequence, which, when contacted with a host cell permissive for influenza virus replication optionally results in recombinant virus. In one embodiment, the DNA of interest is in an antisense orientation. The DNA of interest, whether in a vector for vRNA or protein production, may encode an immunogenic epitope, such as an epitope useful in a cancer therapy or vaccine, or a peptide or polypeptide useful in gene therapy.

A plurality of the vectors of the invention may be physically linked or each vector may be present on an individual plasmid or other, e.g., linear, nucleic acid delivery vehicle.

The invention also provides a method to prepare influenza virus. The method comprises contacting a cell, e.g., an avian or a mammalian cell, with the isolated virus of the invention or a plurality of the vectors of the invention, e.g., sequentially or simultaneously, for example, employing a composition comprising a plurality of the vectors, in an amount effective to yield infectious influenza virus. The invention also includes isolating virus from a cell infected with the virus or contacted with the vectors and/or composition. The invention further provides a host cell infected with the virus of the invention or contacted with the composition or vectors of the invention. In one embodiment, a host cell is infected with an attenuated (e.g., cold adapted) donor virus and a virus of the invention to prepare a cold-adapted reassortant virus useful as a cold-adapted live virus vaccine.

The invention also provides a method to induce an immune response in a mammal, e.g., to immunize a mammal, against one more pathogens, e.g., against a virus of the invention and optionally a bacteria, a different virus, or a parasite or other antigen. An immunological response to a composition or vaccine is the development in the host organism of a cellular and/or antibody-mediated immune response to a viral polypeptide, e.g., an administered viral preparation, polypeptide or one encoded by an administered nucleic acid molecule, which can prevent or inhibit infection to that virus or a closely (structurally) related virus. Usually, such a response consists of the subject producing antibodies, B cell, helper T cells, suppressor T cells, and/or cytotoxic T cells directed specifically to an antigen or antigens included in the composition or vaccine of interest. The method includes administering to the host organism, e.g., a mammal, an effective amount of the influenza virus of the invention, e.g., an attenuated, live virus, optionally in combination with an adjuvant and/or a carrier, e.g., in an amount effective to prevent or ameliorate infection of an animal such as a mammal by that virus or an antigenically closely related virus. In one embodiment, the virus is administered intramuscularly while in another embodiment, the virus is administered intranasally. In some dosing protocols, all doses may be administered intramuscularly or intranasally, while in others a combination of intramuscular and intranasal administration is employed. The vaccine may further contain other isolates of influenza virus including recombinant influenza virus, other pathogen(s), additional biological agents or microbial components, e.g., to form a multivalent vaccine. In one embodiment, intranasal vaccination with inactivated equine influenza virus and a mucosal adjuvant, e.g., the non-toxic B chain of cholera toxin, may induce virus-specific IgA and neutralizing antibody in the nasopharynx as well as serum IgG.

The equine influenza vaccine may employed with other anti-virals, e.g., amantadine, rimantadine, and/or neuraminidase inhibitors, e.g., may be administered separately in conjunction with those anti-virals, for instance, administered before, during and/or after.

Further provided is a diagnostic method which employs a virus of the invention, an isolated viral protein encoded thereby, or antisera specific for the virus or protein, to detect viral specific antibodies or viral specific proteins.

BRIEF DESCRIPTION OF THE FIGURES

FIGS. 1A-1R. Sequences of A/Equine/Wisconsin/1/03. SEQ ID NOs:1-8, 17 and 18 represent the deduced amino acid sequence for HA, NA, PB1, PB2, PA, NP, M1, NS1, M2, and NS2, respectively, of A/Equine/Wisconsin/1/03. SEQ ID NOs:9-16 represent the mRNA sense nucleotide sequence for HA, NA, PB1, PB2, PA, NP, M (M1 and M2) and NS (NS1 and NS2), respectively, of A/Equine/Wisconsin/1/03.

FIG. 2. Sequence alignment of HA-1 of A/Equine/NewYork/99 (SEQ ID NO:19) and A/Equine/Wisconsin/1/03 (SEQ ID NO:20).

DETAILED DESCRIPTION OF THE INVENTION

Definitions

As used herein, the term "isolated" refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture and propagation, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Influenza Virus Type A Structure and Propagation

Influenza A viruses possess a genome of eight single-stranded negative-sense viral RNAs (vRNAs) that encode at least ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cRNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Any cell, e.g., any avian or mammalian cell, such as a human, canine, bovine, equine, feline, swine, ovine, mink, e.g., MvLu1 cells, or non-human primate cell, including mutant cells, which supports efficient replication of influenza virus can be employed to isolate and/or propagate influenza viruses. Isolated viruses can be used to prepare a reassortant virus, e.g., an attenuated virus. In one embodiment, host cells for vaccine production are those found in avian eggs. In another embodiment, host cells for vaccine production are continuous mammalian or avian cell lines or cell strains. It is preferred to establish a complete characterization of the cells to be used, so that appropriate tests for purity of the final product can be included. Data that can be used for the characterization of a cell includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. Preferably, the passage level, or population doubling, of the host cell used is as low as possible.

It is preferred that the virus produced by the host cell is highly purified prior to vaccine or gene therapy formulation. Generally, the purification procedures result in the extensive removal of cellular DNA, other cellular components, and adventitious agents. Procedures that extensively degrade or denature DNA can also be used.

Equine Influenza Virus Detection

Disease causing equine influenza viruses are generally Type A influenza viruses of the H7N7 (equi-1) and H3N8 (equi-2) subtypes. These generally differ from the subtypes that cause infection in man (H1N1, H2N2 and H3N2). Equine influenza is contracted by either inhalation or contact with secretions (e.g., physiological fluid) containing live virus. The virus infects the epithelial cells of the upper and lower airways and can cause deciliation of large areas of the respiratory tract within 4 to 6 days. As a result, the mucociliary clearance mechanism is compromised and tracheal clearance rates may be reduced for up to 32 days following infection. Bronchitis and bronchiolitis develop followed by interstitial pneumonia accompanied by congestion, edema and leukocyte infiltration. In general, H3N8 viruses cause more severe disease than H7N7 viruses; viruses of the H3N8 subtype are more pneumotropic and have also been associated with myocarditis.

Clinical signs in previously influenza-naïve animals are easily recognizable. Influenza is characterized by its sudden onset with an incubation period of 1 to 3 days. The first sign is an elevation of body temperature (up to 41° C.), which is usually biphasic. This is followed by a deep dry cough that releases large quantities of virus into the atmosphere often accompanied by a serous nasal discharge, which may become mucopurulent due to secondary bacterial infection. The other most commonly observed clinical signs are myalgia, inappetance, and enlarged submandibular lymph nodes. Edema of the legs and scrotum is observed very rarely. The severity of the disease varies with the dose and strain of virus and the immune status of the horse.

Previously healthy, immunocompetent adult horses usually recover from uncomplicated influenza within 10 days, although coughing may persist for longer. If secondary bacterial infection occurs, it can prolong the recovery period. However, relatively high mortality rates have been recorded in foals, animals in poor condition and donkeys. If maternal antibody is absent at the time of exposure, young foals may develop a viral pneumonia leading to death. Deaths among adult animals are usually a consequence of secondary bacterial infection leading to pleuritis, suppurative pneumonia or rarely, purpura haemorrhagica. Sequelae of equine influenza can include chronic pharyngitis, chronic bronchiolitis, myocarditis, and alveolar emphysema, which can contribute to heaves, and secondary sinus and guttural pouch infections.

Clinical signs in animals partially immune as a result of vaccination or previous infection are more difficult to recognize as there may be little or no coughing or pyrexia. Whereas spread of infection throughout a group of naïve animals is always rapid, there have been outbreaks in which the infection circulated subclinically in vaccinated horses for 18 days before inducing recognizable clinical signs.

Outbreaks of infectious respiratory disease may be caused by various agents, including equine herpes viruses, rhinoviruses, adenoviruses, and arteritis viruses, *Streptococcus equi*, or *S. zooepidemicus*. A presumptive diagnosis of influenza based on clinical signs should be confirmed by virus isolation or detection, or by serological testing. Laboratory confirmation of a clinical diagnosis may be by traditional isolation of virus from nasopharyngeal swabs or serology to demonstrate seroconversion, or by rapid diagnostic tests which detect the presence of viral antigens, viral nucleic acid, or virally infected cells in respiratory secretions. Rapid diagnostic tests, despite their convenience and ease of use, provide little or no information about genetic or antigenic characteristics of the infecting strain of virus and do not allow isolation of the virus.

Nasopharyngeal swabs for virus isolation or detection should be taken as promptly as possible. Results of experimental challenge studies suggest that peak viral titers are obtained during the initial 24 to 48 hours of fever, on the second or third day after infection, and the duration of viral shedding is usually not more than 4 or 5 days. Nasal swab samples are taken by passing a swab as far as possible into the horse's nasopharynx via the ventral meatus to absorb respiratory secretions. Swabs should be transferred immediately to a container with virus transport medium and transported on ice to maintain viability of the virus. Virus is unlikely to survive if dry swabs are taken and there is an increased chance of contamination if bacterial transport medium is used. Nasal swab samples may be inoculated into the allantoic (or amniotic) cavity of 9- to 11-day-old embryonated hens' eggs. After incubation at 33-35° C. for 3 days, the allantoic fluid is harvested and tested for haemagglutinating activity. Alternatively, cell culture may be used to isolate viruses. Influenza infection can also be diagnosed by comparison of the results of serological testing of an acute serum sample taken as soon as possible after the onset of clinical signs and a convalescent serum sample taken 2 to 4 weeks later.

The haemagglutination inhibition (HI) test measures the capacity of influenza-specific antibody present in serum samples to inhibit the agglutination of red blood cells by virus. Sera are heat-inactivated and pre-treated to reduce non-specific reactions and serially diluted prior to incubation with a standard dose of virus in a U-bottomed microtiter plate. A suspension of red blood cells is added and, after a further incubation period, examined for agglutination. A four-fold rise in virus-specific antibodies indicates infection. Whole virus antigen may be used for H7N7 viruses, but Tween 80-ether disrupted antigen is usually required to enhance the sensitivity of the assay for H3N8 viruses. In repeatedly vaccinated horses, infection may fail to stimulate a 4-fold increase in HI titer.

The single-radial haemolysis (SRH) test, although less strain-specific, is more reproducible and less error prone than the HI test and, as it is a linear test, is more sensitive, enabling detection of smaller increases in antibody induced by infection in heavily vaccinated horses. The SRH test is based on the ability of influenza-specific antibodies to lyse virus-coated red blood cells in the presence of complement. Test sera are added to wells punched in agarose containing coated red blood cells and complement and allowed to diffuse through the agarose for 20 hours. The areas of clear zones of haemolysis around the wells are proportional to the level of influenza antibody present in the serum samples.

If horses are vaccinated in the face of infection, it may not be possible, using the HI and SRH assays, to determine whether any increase in antibody levels is due to vaccination or infection.

Influenza Vaccines

A vaccine of the invention includes an isolated influenza virus of the invention, and optionally one or more other isolated viruses including other isolated influenza viruses, West Nile virus, equine herpes virus, equine arteritis virus, equine infectious anemia lentivirus, rabies virus, Eastern and/or Western and/or Venezuelan equine encephalitis virus, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. It is inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, then purified by a method such as that described by Grand and Skehel (1972).

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

Inactivated Vaccines.

Inactivated influenza virus vaccines are provided by inactivating replicated virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines.

Live, attenuated influenza virus vaccines can be used for preventing or treating influenza virus infection. Attenuation may be achieved in a single step by transfer of attenuated genes from an attenuated donor virus to a replicated isolate or reassorted virus according to known methods (see, e.g., Murphy, 1993). Since resistance to influenza A virus is mediated primarily by the development of an immune response to the HA and/or NA glycoproteins, the genes coding for these surface antigens must come from the reassorted viruses or clinical isolates. The attenuated genes are derived from the attenuated parent. In this approach, genes that confer attenuation preferably do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C., (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene (Subbarao et al., 1993). Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals (Enami et al., 1990; Muster et al., 1991; Subbarao et al., 1993).

It is preferred that such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The virus can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and nucleic acid screening (such as probe hybridization or PCR) to confirm that donor genes encoding the antigenic determinants (e.g., HA or NA genes) are not present in the attenuated viruses. See, e.g., Robertson et al., 1988; Kilbourne, 1969; Aymard-Henry et al., 1985; Robertson et al., 1992.

Pharmaceutical Compositions

Pharmaceutical compositions of the present invention, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. See, e.g., Berkow et al., 1987; Avery's Drug Treatment, 1987; Osol, 1980. The composition of the invention is generally presented in the form of individual doses (unit doses).

Conventional vaccines generally contain about 0.1 to 200 µg, e.g., 30 to 100 µg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents. See, e.g., Berkow et al., 1992; Avery's, 1987; and Osol, 1980.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized. Examples of materials suitable for use in vaccine compositions are provided in Osol (1980).

Heterogeneity in a vaccine may be provided by mixing replicated influenza viruses for at least two influenza virus strains, such as 2-20 strains or any range or value therein. Influenza A virus strains having a modern antigenic composition are preferred. Vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thio semicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, an attenuated or inactivated viral vaccine is provided upon the detection of a symptom or clinical sign of actual infection. The therapeutic administration of the compound(s) serves to attenuate any actual infection. See, e.g., Berkow et al., 1992; and Avery, 1987. When provided therapeutically, a gene therapy composition is provided upon the detection of a symptom or clinical sign of the disease. The therapeutic administration of the compound(s) serves to attenuate a symptom or clinical sign of that disease.

Thus, an attenuated or inactivated vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration

A composition of the present invention may confer resistance to one or more pathogens, e.g., one or more influenza virus strains, by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

At least one influenza virus isolate of the present invention, including one which is inactivated or attenuated, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism can be from about $10^2$-$10^{15}$, e.g., $10^3$-$10^{12}$, plaque forming units (PFU)/kg, or any range or value therein. The dose of inactivated vaccine can range from about 0.1 to 1000, e.g., 30 to 100 µg, of HA protein. However, the dosage should be a safe and effective amount as determined by conventional methods, using existing vaccines as a starting point.

The dosage of immunoreactive HA in each dose of replicated virus vaccine can be standardized to contain a suitable amount, e.g., 30 to 100 µg or any range or value therein, or the amount recommended by government agencies or recognized professional organizations. The quantity of NA can also be standardized, however, this glycoprotein may be labile during purification and storage.

Compositions and Dosing for Equine Influenza Vaccines

Equine influenza vaccines generally include representative strains of H7N7 and H3N8 subtypes either as inactivated whole virus or their subunits. They provide protection against influenza by inducing antibody to the surface glycoproteins, in particular to HA, which is essential for viral attachment and entry into cells, and/or potentially important cell-mediated immune responses to other viral proteins. Vaccination is helpful in preventing influenza but the protection is short-lived (3-4 months using conventional inactivated virus vaccines), so the frequency of vaccination varies according to how often the horse will likely come in contact with the virus (see Table 1). The usual procedure for the primary course is vaccination with a single dose followed 3 to 6 weeks later with a second dose. Vaccine manufacturers recommend that booster vaccinations be given at 6- to 12-month intervals thereafter. Alternatively, a horse is administered one 1 to 2 ml dose, e.g., via intramuscular (IM) injection, a second 1 to 2 ml dose 3 to 4 weeks later at a different injection site, e.g., via IM injection, and optionally a third 1 to 2 ml dose, e.g., IM or intranasal (IN) administration. Each 1 to 2 ml dose of vaccine may contain approximately 1-500 billion virus particles, and preferably 100 billion particles. Horses in contact with a large number of horses, for example, at a boarding stable, training centers, racetracks, shows, and other such events, are often vaccinated every 2-3 months. A three-dose primary series has been shown to induce a higher and more persistent immunity than the recommended two-dose series regardless of the age.

Using conventional vaccines, it is advisable to vaccinate young horses, particularly racehorses and other competition horses, at 4 to 6 month intervals for several years after their primary course of vaccinations. It has been demonstrated that inclusion of an additional booster vaccination between the second and third vaccination recommended by the vaccine manufacturers is of benefit to young horses. An annual booster will usually suffice for older horses such as show jumpers and brood mares that have been vaccinated regularly since they were foals. Vaccination in the face of an ongoing outbreak is sometimes practiced, but is not likely to be effective without an interval of at least 7 to 10 days before the freshly vaccinated horses are exposed to infection. Equine influenza outbreaks are not seasonal as in man but are frequently associated with sales or race meets where horses from different regions congregate and mix. It may therefore be advantageous to time additional booster vaccinations to be given prior to such events.

Brood mares should be vaccinated in the later stages of pregnancy, but not later than 2 weeks prior to foaling, to ensure a good supply of colostral antibodies for the foal. Foal vaccinations should begin at 3-6 months of age, with a booster at 4-7 months, again at 5-8 months, and repeated every three months if the foal is at high risk of exposure.

TABLE 1

| | Foals & Weanlings from Vaccinated Mares | Foal & Weanlings from non-Vaccinated Mares | Yearlings | Performance Horse | Pleasure Horses | Brood-mares |
|---|---|---|---|---|---|---|
| Influenza inactivated injectable | 1st Dose: 9 months 2nd Dose: 10 months 3rd Dose: 11-12 months Then at 3 month intervals | 1st Dose: 6 months 2nd Dose: 7 months 3rd Dose: 8 months Then at 3 month intervals | Every 3-4 months | Every 3-5 months | Annual with Boosters prior to likely exposure | At least semi-annual, with 1 Booster 4-6 weeks prepartum |
| Influenza intranasal cold-adapted live virus | 1st Dose: 12 months; has been safely administered to foals less than 11 months | 1st Dose: 12 months; has been safely administered to foals less than 11 months | Every 4-6 months | Every 4-6 months | Every 4-6 months | Annual before breeding |

Influenza vaccines may be combined with tetanus or herpesvirus antigens as well as other pathogens, e.g., equine pathogens. The immune response elicited by tetanus toxoid is much more durable than that induced by influenza antigen. In an intensive influenza vaccination program, vaccines containing influenza only are thus preferred.

Levels of antibody (measured by the SRH assay) required for protection of horses have been identified through vaccination and challenge studies and from field data. Because the vaccine-induced antibody response to HA in horses is remarkably short-lived, adjuvants such as aluminum hydroxide or carbomer are normally included to enhance the amplitude and duration of the immune response to whole virus vaccines. Subunit equine influenza vaccines containing immune stimulating complexes (ISCOMs) are also immunogenic.

Historically, antigenic content in inactivated vaccines has been expressed in terms of chick cell agglutinating (CCA) units of HA and potency in terms of HI antibody responses induced in guinea pigs and horses, neither of which yields reproducible results. The single radial diffusion (SRD) assay is an improved in vitro potency test that measures the concentration of immunologically active HA (expressed in terms of micrograms of HA) and can be used for in-process testing before the addition of adjuvant.

The invention will be further described by the following non-limiting example.

EXAMPLE

An approximately 36-hour-old Morgan/Friesian colt was referred to the large animal hospital at the University of Wisconsin for an evaluation of altered mentation (mental status), first noticed shortly after birth. Parturition had been unobserved, but the foal had been found separated from the mare by a fence at a few hours of age. The foal was ambulatory and able to nurse when first discovered but showed progressive disorientation, apparent blindness, and aimless wandering during the following 36-hour period. A SNAP immunoglobulin G (IgG) assay (Idexx Laboratories, Westbrook, Me.) at 24 hours of age had shown an IgG concentration >800 mg/dL, and a CBC performed at that time was normal. The foal was treated twice with dimethyl sulfoxide 1 g/kg IV, diluted in 5% dextrose before referral.

At presentation, the colt wandered aimlessly, bumped into objects, and appeared blind with sluggish but intact pupillary light responses. When positioned under the mare, the foal nursed successfully. Physical examination was unremarkable. A CBC and serum biochemistry were normal, including a serum IgG concentration of 937 mg/dL measured by radioimmunodiffusion.

Initial treatment for presumptive hypoxemic, ischemic encephalopathy included a 250 mL loading dose of 20% magnesium sulfate for 1 hour, followed by a constant rate infusion at 42 mL/h and thiamine hydrochloride 2.2 mg/kg IV q24h. Antimicrobial therapy consisted of amikacin 20 mg/kg IV q24h and procaine penicillin G 22,000 U/kg IM q12h. Omeprazole 1 mg/kg PO q24h also was administered to the foal to help prevent the development of gastric ulcers.

The foal's mental status remained static during the next 24 hours, and additional treatment with mannitol 1 g/kg IV q24h and dexamethasone sodium phosphate 0.1 mg/kg IV q24h on days 2 and 3 of hospitalization was not associated with improvement. On day 3, the foal underwent general anesthesia for a computerized tomographic scan of the skull and proximal spine, which was normal. A cerebrospinal fluid sample was obtained from the lumbosacral space and was normal on cytologic evaluation and had a normal protein concentration.

On day 4 of hospitalization, the foal developed a right-sided head tilt but otherwise remained static through day 5 of hospitalization. Magnesium sulfate therapy was discontinued on day 5, but the remainder of the therapeutic regimen was unchanged. On day 6, the foal had 2 brief, generalized seizures that were controlled with midazolam 0.05 mg/kg IV. Between seizures, the foal was still bright, afebrile, and nursing.

On day 7 of hospitalization, the foal became febrile (40° C.) and developed a mucopurulent nasal discharge and progressive tachypnea with diffuse adventitious crackles and wheezes on auscultation. Fever, mucopurulent nasal discharge, and coughing had been noted in several other mares and foals in the neonatal care unit during the previous 7 days. Antimicrobial therapy was changed to ticarcillin/clavulanic acid 50 mg/kg IV q8h had gentamicin 6.6 mg/kg IV q24h, and the foal was treated with polyionic fluids, although it was still nursing. During days 8-10, the foal's neurologic status continued to improve, with a resolution of the head tilt and a return to normal mentation, but the tachypnea, dyspnea, and adventitious lung sounds worsened. Thoracic radiography at this time showed a severe, diffuse bronchointerstitial pattern. Aminophylline 0.5 mg/kg IV q12h by slow infusion and nasal insufflation of oxygen were instituted on days 9 and 10 of hospitalization. Serial arterial blood gas analysis identified severe hypoxemia (PaO$_2$, 52 mm Hg), hypercapnia (PaCO$_2$, 68.4 mm Hg), and reduced oxygen saturation (76%) by the end of day 10. Consequently, the foal was placed on a mechanical ventilator. Ventilatory support and total parenteral nutrition were continued for 48 hours, during which time arterial blood gas values normalized on 100% oxygen. Antimicrobial therapy was continued as before. When challenged on day 13 by the removal of ventilatory support, the foal developed severe dyspnea and cyanosis and was euthanized at the owner's request. An aerobic culture of a transtracheal aspirate obtained on day 13 grew *Klebsiella pneumoniae* and *Escherichia coli* resistant to ticarcillin/clavulanic acid and gentamicin.

A complete gross and histopathologic postmortem examination was performed, as well as a real-time quantitative polymerase chain reaction (PCR) evaluation for the presence of equine herpes virus (EHV)-1 and EHV-4 in samples of nasal secretions; serologic tests to determine if there was exposure to equine viral arteritis virus; and a Directigen Flu A assay (Bectin Dickinson and Co., Franklin, N.J.) and virus isolation from samples of nasal secretions to test for the presence of influenza virus. Samples of nasal secretions were collected with Dacron swabs that were subsequently placed in 2 mL of viral transport media containing phosphate-buffered saline, 0.5% bovine serum albumin, and penicillin G, streptomycin, nystatin, and gentamicin. The nasal swab samples were collected on day 8 of hospitalization. Followup evaluations for the influenza virus included immunohistochemistry on snap-frozen and formalin-fixed lung, abdominal viscera, and central nervous system tissues for the presence of influenza nucleoprotein (NP) expression, virus isolation from frozen lung tissue, and viral sequence analyses. Gross post-mortem examination identified severe diffuse interstitial pneumonia and subdural hemorrhage on the caudal ventral surface of the brain around the pituitary gland but no evidence of sepsis or pathology in other organs. Histopathologic examination of the lung identified necrotizing bronchitis and brochiolitis, diffuse squamous metaplasia, and multifocal interstitial pneumonia. A mild mononuclear infiltrate lined the lower airways and, occasionally, areas of alveolar collapse associated with congestion and exudate. Evaluation of the brain tissue revealed a mild dilatation of the ventricular system with diffuse white matter vacuolation, particularly in the cerebellum. Cresyl violet staining for the presence of myelin was performed on multiple sections and showed diminished but present myelin throughout the brain and spinal cord when compared to tissues from an age-matched control stained in parallel. Additional histopathologic abnormalities in the central nervous system included an apparent absence of the molecular layer within the cerebellum. Serologic tests for equine viral arteritis and a real-time PCR assay for EHV-1 and EHV-4 DNA were negative.

The presence of influenza virus in nasal secretions initially was confirmed by a positive Directigen assay. Previous studies have documented the sensitivity and specificity of this assay when applied to equine nasal secretion samples (Morely et al., 1995 and Chambers et al., 1994). Samples of the nasal swab transport media also were inoculated into the allantoic cavity of embryonated chicken eggs and onto Madin-Darby canine kidney (MDCK) cells growing in 24-well cell culture plates. Cytopathologic effects consistent with influenza virus growth were observed in the inoculated MDCK cells, and an agent that caused the hemagglutination of chicken red blood cells was isolated from the inoculated eggs (Palmar et al., 1975). The presence of influenza virus in the MDCK cell cultures was confirmed by the immunocytochemical staining (Landolt et al., 2003) of the inoculated cells with an anti-NP monoclonal antibody (Mab) 68D2 (kindly provided by Dr. Yoshihiro Kawaoka, University of Wisconsin-Madison School of Veterinary Medicine) with positive (swine influenza virus inoculated) and negative (mock inoculated) control cells included on the same plate. The identity of the virus as an H3-subtype equine influenza virus was confirmed by reverse transcription-PCR amplification of the hemagglutinin (HA) gene from the isolate, with primers described in Olsen et al. (1997), followed by cycle sequencing of the full-length protein coding region of the HA gene and pairwise comparisons to viral sequences available in GenBank (DNASTAR software, version 4.0 for Win32, Bestfit, Madison, Wis.). The virus was shown to be derived from the North American lineage of H3 equine influenza viruses by a phylogenetic analysis that used a maximum parsimony bootstrap analysis (PAUP software, version 4.0b6; David Swofford, Smithsonian Institution, Washington, D.C.) of the HA sequence compared to reference virus strains with a fast-heuristic search of 1,000 bootstrap replicates. Similar analyses of portions of the nucleotide sequences of the nonstructural protein gene (544 nucleotides sequenced) and the NP gene (885 nucleotides sequenced) further confirmed the identity of the virus as a North American-lineage equine influenza virus. This virus is now defined as A/Equine/Wisconsin/1/03. FIG. 1 provides sequences for the coding region of each gene of that virus.

The presence of influenza virus also was assessed in the lungs and other tissues of the foal. Specifically, immunohistochemistry with Mab 68D2 showed scattered, widely dispersed areas of influenza virus NP expression (predominantly localized around airways) in the frozen as well as the formalin-fixed lung tissue samples. NP expression was not shown in the other viscera or in the central nervous system. In addition, influenza virus was isolated in MDCK cells (and confirmed by immunocytochemistry and HA gene sequencing) from a sample of the frozen lung tissue.

Acute respiratory distress syndrome (ARDS) in neonatal foals has been documented as a consequence of bacterial sepsis (Wilkins, 2003; Hoffman et al., 1993), perinatal EHV-1 (Frymus et al., 1986; Gilkerson et al., 1999) and EHV-4 (Gilkerson et al., 1999), and equine viral arteritis infection (Del Piero et al., 1997). Less severe lower airway disease occasionally is documented with adenovirus and EHV-2 infections, particularly in the immunocompromised patient (Webb et al., 1981; Murray et al., 1996). Bronchointerstitial pneumonia and ARDS are high-mortality respiratory diseases of older foals with several potential causes, including bacterial and viral infections (Lakritz et al., 1993). Whether it occurs in neonates experiencing septic shock or in older foals with diffuse bronchointerstitial pneumonia, ARDS is characterized by acute-onset, rapidly progressive, severe tachypnea. The increased respiratory effort, worsening cyanosis, hypoxemia, and hypercapnia that accompany ARDS frequently are poorly responsive to aggressive therapy (Wilkins, 2003; Lakritz et al., 1993). It is a category of respiratory disease with several potential etiologies and a mortality rate that frequently exceeds 30% despite intensive treatment with antimicrobials, oxygen, anti-inflammatory agents, brochodilators, and thermoregulatory control. Equine influenza is a well-documented cause of upper respiratory disease in horses worldwide (Wilkins, 2003; Van Maanen et al., 2002; Wilson, 1993), but very little information exists in the literature about the manifestations of this disease in neonates. A single report describes bronchointerstitial pneumonia in a 7-day-old foal from which equine influenza A was isolated (Britton et al., 2002); this foal resembles the foal described herein.

The foal detailed in this study was one of several hospitalized horses that developed fever, mucopurulent nasal discharge, and coughing during a 2- or 3-week period. Clinical signs in the other affected horses, including high-risk neonates, generally were confined to the upper respiratory tract, except for mild systemic signs of fever and inappetance. The reason for the severity of the pulmonary failure in this foal is unclear. Treatment did include the potentially immunosuppressive drug dexamethasone and general anesthesia for a diagnostic procedure, both of which may have predisposed the foal to the development of pneumonia. The impact of the foal's neurologic disease on the development and progression of respiratory disease also is unclear. The histologic findings of diffuse vacuolization, decreased myelin throughout the central nervous system, and absent molecular layer within the cerebellum do not fit any specific clinical or histopathologic diagnosis. The foal could have had impaired central control of respiration, because the areas of the brain involved in the control of respiration (the pons and medulla oblongata) showed diffuse vacuolization and diminished myelin staining. Any subsequent impairment of ventilation would likely have been a terminal event given the normalcy of ventilatory function until several days after hospitalization. However, the abnormal mentation from birth, the vacuolization, the decreased myelinization in the central nervous system, and the cerebellar abnormalities are suggestive of a concurrent, congenital neurologic abnormality, which may have compromised the foal's ability to respond to worsening respiratory function. The focal hemorrhage observed on the caudal ventral aspect of the brain was mild and was possibly a consequence of trauma during one of the seizures the foal experienced.

The mare had been vaccinated semiannually against influenza for the past 2 years with a killed product and was given a booster vaccination in late pregnancy. Considering the evidence of adequate passive transfer in this foal, these antibodies apparently did not confer adequate protection for the foal. Furthermore, phylogenetic analysis of the isolate obtained from the foal characterized it as an H3N8 subtype, and the commercial product used to vaccinate the mare in late pregnancy contained an influenza virus strain of the same subtype, suggesting that passive transfer cannot be guaranteed to protect against natural infection under certain circumstances. This lack of vaccine efficacy is consistent with a recent study by Mumford et al. (2003) that describes the failure of commercially available H7N7 and H3N8 equine influenza virus vaccines to protect adults against clinical respiratory disease that results from a natural infection with certain H3N8 virus strains. The transtracheal recovery of 2 bacterial species that were resistant to the antimicrobial regimen in place at the time of death confounds the conclusion that influenza was the sole cause of death. However, postmortem examination identified no gross or histopathologic evidence of sepsis, and synergism occurs between the influenza virus and some bacterial pathogens, combining to cause pneumonia with increased mortality (McCullers et al., 2003; Simonsen, 1999). Furthermore, the isolation of the infectious virus and the immunohistochemical demonstration of viral antigen from the lung tissue obtained postmortem, 6 days after the virus initially was recovered by a nasopharyngeal swab, provide strong evidence of a pathologic contribution from influenza virus in this foal's respiratory failure.

To compare the growth characteristics of avian, equine, human, and porcine lineage viruses in primary canine respiratory epithelial cells and to investigate the species influence on their growth characteristics, cultured cells were infected at an MOI of 3 with viruses including A/Equine/Wisconsin/1/03 and incubated for up to 10 hours. The other viruses included six human and swine influenza A virus isolates (A/Phillipines/08/98, A/Panama/2002/99, A/Costa Rica/07/99; A/Swine/NorthCarolina/44173/00, A/Swine/Minnesota/593/99, A/Swine/Ontario/00130/97, and two equine influenza viruses (A/Equine/Kentucky/81 and A/Equine/Kentucky/91). At the end of the experiment, the cells were formalin fixed for immunocytochemistry and flow cytometry analyses.

The six human and swine influenza virus isolates mentioned above readily infected substantially all (80-90%) of the canine respiratory epithelial cells and grew to high titers ($10^{5.3}$-$10^7$ $TCID_{50}$/ml) in those cells. A/Equine/Kentucky/81 and A/Equine/Kentucky/91 were highly restricted in their infectivity (<10% of the cells infected) with little ($10^{1.7}$ $TCID_{50}$/ml for A/Equine/Kentucky/81) or no (for A/Equine/Kentucky/91) detectable viral growth. In contrast, A/Equine/Wisconsin/1/03 infected a larger percentage (about 30%) of the primary canine respiratory epithelial cells and grew to substantially higher titers (about $10^{4.8}$ $TCID_{50}$/ml) in those cells. The results demonstrated that all influenza A viruses tested were able to infect canine primary respiratory epithelial cells. However, the infectivity and replication characteristics of the viruses were strongly lineage-dependent.

Dubovi et al. (2004) noted recurrent outbreaks of severe respiratory disease characterized by coughing and fever in greyhound dogs at racing kennels in Florida. Most affected dogs recovered, but some succumbed to a fatal hemorrhagic pneumonia. Lung tissues from 5 of the dogs that died from the hemorrhagic pneumonia syndrome were subjected to virus isolation studies in African green monkey kidney epithelial cells (Vero), Madin-Darby canine kidney epithelial cells (MDCK), primary canine kidney epithelial cells, primary canine lung epithelial cells, primary bovine testicular epithelial cells, canine tumor fibroblasts (A-72), and human colorectal adenocarcinoma epithelial cells (HRT-18) (Dubovi et al., 2004). Cytopathology in the MDCK cells was noted on the first passage of lung homogenate from one of the dogs, and the loss of cytopathology upon subsequent passage to cells cultured without trypsin coupled with the presence of hemagglutinating activity in culture supernatants suggested the presence of an influenza virus (Dubovi et al., 2004). The virus was initially identified as influenza virus by PCR using primers specific for the matrix gene. The canine influenza virus has been designated as the A/Canine/Florida/43/04 strain. Based on virus isolation from the lungs, the presence of viral antigens in lung tissues by immunohistochemistry, and seroconversion data, Dubovi et al. (2004) concluded that the isolated influenza virus was most likely the etiological agent responsible for the fatal hemorrhagic pneumonia in racing greyhounds during the Jacksonville 2004 outbreak, and that this was the first report of an equine influenza virus associated with respiratory disease in dogs (Dubovi et al., 2004). The HA protein of the canine isolate differs from the A/Equine/Wisconsin/1/03 strain by only 6 amino acids.

REFERENCES

*Avery's Drug Treatment: Principles and Practice of Clinical Pharmacology and Therapeutics,* 3rd edition, ADIS Press, Ltd., Williams and Wilkins, Baltimore, Md. (1987).

Aymard-Henry et al., *Virology: A Practical Approach*, Oxford IRL Press, Oxford, 119-150 (1985).
Bachmeyer, *Intervirology*, 5:260 (1975).
Berkow et al., eds., *The Merck Manual*, 16th edition, Merck & Co., Rahway, N.J. (1992).
Britton et al., *Can. Vet. J.*, 43:55 (2002).
Chambers et al., *Vet. Rec.*, 135:275 (1994).
Daly and Mumford, In: Equine Respiratory Diseases Lekeux (ed.) International Veterinary Information Science, Ithaca, N.Y. (2001).
Del Piero et al., *Equine Vet. J.*, 29:178 (1997).
Dubovi et al., Proceedings of the American Association of Veterinary Laboratory Diagnostics, p. 158 (2004).
Enami et al., *Proc. Natl. Acad. Sci. U.S.A.*, 87:3802 (1990).
Frymus et al., *Pol. Arch. Med. Wewn*, 26:7 (1993).
Gilkerson et al., *Vet. Microbiol.*, 68:27 (1999).
Grand and Skehel, *Nature, New Biology*, 238:145 (1972).
Hoffman et al., *Am. J. Vet. Res.*, 54:1615 (1993).
Kilbourne, *Bull. M2 World Health Org.*, 41: 653 (1969).
Lakritz et al., *J. Vet. Intern. Med.*, 7:277 (1984-1989).
Landolt et al., *J. Clin. Microbiol.*, 41:1936 (2001).
Laver & Webster, *Virology*, 69:511 (1976).
Marriott et al., *Adv. Virus Res.*, 53:321 (1999).
McCullers et al., *J. Infect. Dis.*, 187:1000 (2003).
Morley et al., *Equine Vet. J.*, 27:131 (1995).
Mumford et al., *Equine Vet. J.*, 35:72 (2003).
Murphy, *Infect. Dis. Clin. Pract.*, 2: 174 (1993).
Murray et al., *Equine Vet. J.*, 28:432 (1996).
Muster et al., *Proc. Natl. Acad. Sci. USA*, 88: 5177 (1991).
Neumann et al., *Proc. Natl. Acad. Sci. U. S. A*, 96:9345 (1999).
Ogra et al., *J. Infect. Dis.*, 134: 499 (1977).
Olsen et al., *Vaccine*, 15:1149 (1997).
Osol (ed.), *Remington's Pharmaceutical Sciences*, Mack Publishing Co., Easton, Pa. 1324-1341 (1980).
Palmar et al., Madison Wis.: University of Wisconsin Department of Health, Education and Welfare Immunology Series (1975).
Park et al., *Proc. R. Soc. London B.*, 271:1547 (2004).
Robertson et al., *Biologicals*, 20:213 (1992).
Robertson et al., *Giornale di Igiene e Medicina Preventiva*, 29:4 (1988).
Simonsen, *Vaccine*, 17:S3 (1999).
Subbarao et al., *J. Virol.*, 67:7223 (1993).
Van Maanen et al., *Vet. Q.*, 24:79 (2002).
Webb et al., *Aust. Vet. J.*, 57:142 (1981).
Wilkins, *Vet. Clin. North Am. Equine Pract.*, 19:19 (2003).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method to immunize a mammal against influenza, comprising administering to the mammal an effective amount of a composition comprising an H3 influenza virus comprising a gene segment with sequences for a HA having SEQ ID NO:1 or a HA having at least 98% amino acid sequence identity to SEQ ID NO:1 which HA does not have a valine at position 78 or an asparagine at position 159.

2. The method of claim 1 wherein the mammal is a dog or a horse.

3. A diagnostic method comprising contacting a physiological sample of an animal suspected of containing anti-influenza virus antibodies with an H3 influenza virus comprising a gene segment with sequences for a HA having SEQ ID NO:1 or a HA having at least 98% amino acid sequence identity to SEQ ID NO:1 which HA does not have a valine at position 78 or an asparagine at position 159; and determining whether the sample comprises antibodies specific for the virus.

4. The method of claim 1 wherein the H3 influenza virus comprises at least one of the following gene segments: a gene segment with sequences for a NA having SEQ ID NO:2 or having at least 95% amino acid sequence identity to SEQ ID NO:2, a gene segment with sequences for a PB1 having SEQ ID NO:3 or having at least 95% amino acid sequence identity to SEQ ID NO:3, a gene segment with sequences for a PB2 having SEQ ID NO:4 or having at least 95% amino acid sequence identity to SEQ ID NO:4, a gene segment with sequences for a PA having SEQ ID NO:5 or having at least 95% amino acid sequence identity to SEQ ID NO:5, a gene segment with sequences for a NP having SEQ ID NO:6 or having at least 95% amino acid sequence identity to SEQ ID NO:6, a gene segment with sequences for a M1 having SEQ ID NO:7 or having at least 95% amino acid sequence identity to SEQ ID NO:7, a gene segment with sequences for a M2 having SEQ ID NO:17 or having at least 95% amino acid sequence identity to SEQ ID NO:17, a gene segment with sequences for a NS1 having SEQ ID NO:8 or having at least 95% amino acid sequence identity to SEQ ID NO:8, or a gene segment with sequences for a NS2 having SEQ ID NO:18 or having at least 95% amino acid sequence identity to SEQ ID NO:18.

5. The method of claim 1 wherein the composition further comprises a different influenza virus.

6. The method of claim 1 wherein the H3 influenza virus is an attenuated virus or is a reassortant virus.

7. The method of claim 1 wherein the H3 influenza virus has been altered by chemical, physical or molecular means.

8. The method of claim 1 wherein the composition further comprises an adjuvant or a pharmaceutically acceptable carrier.

9. The method of claim 8 wherein the carrier is suitable for intranasal or intramuscular administration.

* * * * *